United States Patent
Seward et al.

[11] Patent Number: 6,129,672
[45] Date of Patent: *Oct. 10, 2000

[54] VOLUMETRIC IMAGE ULTRASOUND TRANSDUCER UNDERFLUID CATHETER SYSTEM

[75] Inventors: James Bernard Seward; Abdul Jamil Tajik, both of Rochester, Minn.

[73] Assignee: Mayo Foundation for Medical Education and Research, Rochester, Minn.

[*] Notice: This patent is subject to a terminal disclaimer.

[21] Appl. No.: 09/003,248

[22] Filed: Jan. 6, 1998

Related U.S. Application Data

[63] Continuation of application No. 08/678,380, Jun. 28, 1996, Pat. No. 5,704,361, which is a continuation-in-part of application No. 08/305,138, Sep. 13, 1994, abandoned, which is a continuation of application No. 07/972,626, Nov. 6, 1992, Pat. No. 5,345,940, which is a continuation-in-part of application No. 07/790,580, Nov. 8, 1991, Pat. No. 5,325,860.

[51] Int. Cl.[7] ............................................... A61B 8/12
[52] U.S. Cl. ............................................. 600/463; 128/916
[58] Field of Search .......................... 600/439, 443–446, 600/462–463, 471; 129/916; 606/159, 169

[56] References Cited

U.S. PATENT DOCUMENTS

| | | |
|---|---|---|
| 3,789,833 | 2/1974 | Bom . |
| 3,817,089 | 6/1974 | Eggleton et al. . |
| 3,938,502 | 2/1976 | Bom . |
| 4,028,934 | 6/1977 | Sollish . |
| 4,110,723 | 8/1978 | Hetz et al. . |
| 4,354,502 | 10/1982 | Colley et al. . |
| 4,374,525 | 2/1983 | Baba . |
| 4,391,282 | 7/1983 | Ando et al. . |
| 4,462,408 | 7/1984 | Silverstein et al. . |
| 4,466,444 | 8/1984 | Baba . |
| 4,543,960 | 10/1985 | Harui et al. ............................. 128/660 |
| 4,550,607 | 11/1985 | Maslak et al. ............................. 73/626 |

(List continued on next page.)

FOREIGN PATENT DOCUMENTS

| | | |
|---|---|---|
| 0 234 951 A1 | 9/1987 | European Pat. Off. . |
| 0 600 568 | 6/1994 | European Pat. Off. . |
| 0 642 762 A2 | 3/1995 | European Pat. Off. . |
| 44 23 808 A1 | 1/1995 | Germany . |
| WO 90/13260 | 11/1990 | WIPO . |
| WO 91/04707 | 4/1991 | WIPO . |
| WO 93/08738 | 5/1993 | WIPO . |
| WO 94/16625 | 8/1994 | WIPO . |
| WO 95/19143 | 7/1995 | WIPO . |
| WO 96/00522 | 1/1996 | WIPO . |
| WO 96/03918 | 2/1996 | WIPO . |
| WO 96/03921 | 2/1996 | WIPO . |
| WO 96/03922 | 2/1996 | WIPO . |
| WO 96/04588 | 2/1996 | WIPO . |

OTHER PUBLICATIONS

Weintraub et al., "Realtime Intracardiac Two–Dimensional Echocardiography in the Catheterization Laboratory in Humans". Abstract *JACC* vol. 15, No. 2, 16A (Feb. 1990).

(List continued on next page.)

*Primary Examiner*—Francis J. Jaworski
*Attorney, Agent, or Firm*—Merchant & Gould P.C.

[57] ABSTRACT

An underfluid ultrasound imaging catheter system includes a catheter having a distal end inserted into an underfluid structure, an ultrasonic transducer array mounted proximate the distal end of the catheter wherein the array has a row of individual transducer crystals, a lens mounted on the array for defocusing ultrasound beams in a direction perpendicular to an axis of the array so as to provide a volumetric field of view within which the underfluid features are imaged. Alternatively, the single row of transducer crystals is replaced by multiple rows of transducer crystals so as to provide a volumetric field of view. This imaging catheter system helps an operator see 3-dimensional images of an underfluid environment, such as the 3-dimensional images of fluid-filled cavities of heart, blood vessel, urinary bladder, etc. Features in such wide volumetric field of view can be imaged, measured, or intervened by an underfluid therapeutic device with an aid of the real-time image.

19 Claims, 14 Drawing Sheets

U.S. PATENT DOCUMENTS

| | | | |
|---|---|---|---|
| 4,582,067 | 4/1986 | Silverstein et al. | 128/663 |
| 4,699,009 | 10/1987 | Maslak et al. | 73/626 |
| 4,748,985 | 6/1988 | Nagasaki . | |
| 4,756,313 | 7/1988 | Terwilliger . | |
| 4,757,821 | 7/1988 | Snyder . | |
| 4,771,788 | 9/1988 | Millar | 128/661.09 |
| 4,794,931 | 1/1989 | Yock | 128/660.03 |
| 4,802,487 | 2/1989 | Martin et al. . | |
| 4,841,977 | 6/1989 | Griffith et al. | 128/344 |
| 4,841,979 | 6/1989 | Dow et al. . | |
| 4,869,256 | 9/1989 | Kanno et al. . | |
| 4,869,258 | 9/1989 | Hetz . | |
| 4,887,605 | 12/1989 | Angelsen et al. | 128/660.03 |
| 4,911,170 | 3/1990 | Thomas, III et al. | 128/662.06 |
| 4,917,097 | 4/1990 | Proudian et al. | 128/662.06 |
| 4,930,515 | 6/1990 | Terwilliger . | |
| 4,936,281 | 6/1990 | Stasz | 128/660.03 |
| 4,947,852 | 8/1990 | Nassi et al. | 128/662.06 |
| 4,951,677 | 8/1990 | Crowley et al. | 128/662.06 |
| 4,957,111 | 9/1990 | Millar | 128/662.06 |
| 5,000,185 | 3/1991 | Yock . | |
| 5,002,059 | 3/1991 | Crowley et al. | 128/662.06 |
| 5,010,886 | 4/1991 | Passafaro et al. . | |
| 5,014,710 | 5/1991 | Maslak et al. | 128/660.05 |
| 5,022,399 | 6/1991 | Biegeleisen | 128/662.06 |
| 5,029,588 | 7/1991 | Yock et al. | 128/662.06 |
| 5,038,789 | 8/1991 | Frazin | 128/662.06 |
| 5,070,879 | 12/1991 | Herres . | |
| 5,076,278 | 12/1991 | Vilkomerson et al. | 128/662.03 |
| 5,076,279 | 12/1991 | Arenson et al. | 128/662.05 |
| 5,081,993 | 1/1992 | Kitney et al. . | |
| 5,085,221 | 2/1992 | Ingebrigsten et al. . | |
| 5,105,819 | 4/1992 | Wollschläger et al. | 128/662.06 |
| 5,107,844 | 4/1992 | Kami et al. . | |
| 5,115,814 | 5/1992 | Griffith et al. . | |
| 5,125,410 | 6/1992 | Misono et al. . | |
| 5,135,001 | 8/1992 | Sinofsky et al. . | |
| 5,140,558 | 8/1992 | Harrison, Jr. et al. | 367/7 |
| 5,148,810 | 9/1992 | Maslak et al. | 128/661.01 |
| 5,152,294 | 10/1992 | Mochizuki et al. . | |
| 5,159,931 | 11/1992 | Pini . | |
| 5,161,537 | 11/1992 | Hashimoto et al. | 128/662.06 |
| 5,165,413 | 11/1992 | Maslak et al. | 128/660.05 |
| 5,174,296 | 12/1992 | Watanabe et al. . | |
| 5,181,514 | 1/1993 | Solomon et al. . | |
| 5,183,048 | 2/1993 | Eberle . | |
| 5,186,175 | 2/1993 | Hirama et al. . | |
| 5,186,177 | 2/1993 | O'Donnell et al. | 128/662.06 |
| 5,193,546 | 3/1993 | Shaknovich | 128/662.06 |
| 5,199,433 | 4/1993 | Metzger et al. . | |
| 5,199,437 | 4/1993 | Langberg . | |
| 5,211,168 | 5/1993 | Mason et al. . | |
| 5,215,092 | 6/1993 | Wray . | |
| 5,222,501 | 6/1993 | Ideker et al. | 128/660.03 |
| 5,226,422 | 7/1993 | McKeighen et al. . | |
| 5,235,986 | 8/1993 | Maslak et al. | 128/661.01 |
| 5,243,988 | 9/1993 | Siefen et al. | 600/463 |
| 5,257,629 | 11/1993 | Kitney et al. . | |
| 5,261,408 | 11/1993 | Maslak et al. | 128/661.01 |
| 5,285,788 | 2/1994 | Arenson et al. | 128/660.05 |
| 5,291,893 | 3/1994 | Slayton | 128/662.06 |
| 5,295,486 | 3/1994 | Wollschlögen et al. | 128/916 |
| 5,297,553 | 3/1994 | Sliwa, Jr. et al. | 128/662.03 |
| 5,299,578 | 4/1994 | Rotteveel et al. . | |
| 5,305,755 | 4/1994 | Nakao . | |
| 5,305,756 | 4/1994 | Entrekin et al. | 128/660.09 |
| 5,311,871 | 5/1994 | Yock | 128/662.95 |
| 5,313,949 | 5/1994 | Yock . | |
| 5,320,104 | 6/1994 | Fearnside et al. . | |
| 5,325,860 | 7/1994 | Seward et al. | 128/662.06 |
| 5,329,496 | 7/1994 | Smith | 367/140 |
| 5,329,927 | 7/1994 | Gardineer et al. . | |
| 5,343,865 | 9/1994 | Gardineer et al. . | |
| 5,345,940 | 9/1994 | Seward et al. | 600/463 |
| 5,351,691 | 10/1994 | Brommersma . | |
| 5,360,007 | 11/1994 | Shinomura et al. . | |
| 5,373,845 | 12/1994 | Gardineer et al. | 128/660.09 |
| 5,373,849 | 12/1994 | Maroney et al. . | |
| 5,377,685 | 1/1995 | Kazi et al. . | |
| 5,385,148 | 1/1995 | Lesh et al. | 128/662.06 |
| 5,398,689 | 3/1995 | Connor et al. . | |
| 5,402,793 | 4/1995 | Gruner et al. . | |
| 5,415,175 | 5/1995 | Hanafy et al. | 128/662.03 |
| 5,421,336 | 6/1995 | De Bernardis . | |
| 5,425,370 | 6/1995 | Vilkomerson . | |
| 5,437,283 | 8/1995 | Ranalletta et al. | 800/463 |
| 5,438,997 | 8/1995 | Sieben et al. . | |
| 5,438,998 | 8/1995 | Hanafy | 128/662.03 |
| 5,460,181 | 10/1995 | Seyed-Bolorforosh . | |
| 5,464,016 | 11/1995 | Nicholas et al. . | |
| 5,465,724 | 11/1995 | Sliwa, Jr. et al. | 128/662.03 |
| 5,467,779 | 11/1995 | Smith et al. . | |
| 5,469,852 | 11/1995 | Nakamura et al. . | |
| 5,474,075 | 12/1995 | Goldberg et al. . | |
| 5,479,929 | 1/1996 | Cooper et al. . | |
| 5,479,930 | 1/1996 | Gruner et al. . | |
| 5,485,846 | 1/1996 | Webler et al. . | |
| 5,487,388 | 1/1996 | Rello et al. . | |
| 5,499,630 | 3/1996 | Hiki et al. . | |
| 5,503,152 | 4/1996 | Oakley et al. . | |
| 5,549,111 | 8/1996 | Wright et al. | 128/742 |
| 5,562,095 | 10/1996 | Downey et al. . | |
| 5,569,276 | 10/1996 | Jang et al. . | |
| 5,630,416 | 5/1997 | Uchikura et al. . | |
| 5,634,464 | 6/1997 | Jang et al. . | |
| 5,697,377 | 12/1997 | Wittkampf . | |
| 5,699,805 | 12/1997 | Seward et al. . | |
| 5,704,361 | 1/1998 | Seward et al. | 600/463 |
| 5,749,833 | 5/1998 | Hakki et al. . | |

OTHER PUBLICATIONS

Pandian et al., "Intracardiac Echocardiography. Experimental Observations on Intracavitary Imaging of Cardiac Structures with 20–MHz Ultrasound Catheters", *Echocardiography*, vol. 8, No. 1 (Jan. 1991) pp. 127–134.

Seward et al., "Transvascular and Intracardiac Two–Dimensional Echocardiography", *Echocardiography*, vol. 7, No. 4 (Jul. 1990) pp. 457–464.

Schwartz et al., "Real–Time Intracardiac Two–Dimensional Echocardiography: An Experimental Study on In Vivo Feasibility, Imaging, Planes, and Echocardiographic Anatomy", *Echocardiography*, vol. 7, No. 4 (1990) pp. 443–455.

Schwartz et al., "Intracardiac Echocardiography in Humans Using a Small–Sized (6F), Low Frequency (12.5 MHz) Ultrasound Catheter", *JACC*, vol. 21, No. 1 (Jan. 1993) pp. 189–198.

"Cardiovascular Imaging Systems' Intracardiac Imaging Catheter", *M–D–D–I Reports*, publisher: F–D–C Reports, Inc., pp. I&W–6 and I&W–7 (Mar. 30, 1992).

Moriuchi et al., "Transvenous Echocardiography: Experimental Feasibility Study", *Jpn J Med Ultrasonics*, vol. 19, No. 3 (1992), pp. 228–235.

Nishimura et al., "Intravascular Ultrasound Imaging: In Vitro Validation and Pathologic Correlation", *JACC*, vol. 16, No. 1 (Jul. 1990) pp. 142–154.

Pandian et al., "Intracardiac, Intravascular, Two–Dimensional, High–Frequency Ultrasound Imaging of Pulmonary Artery and Its Branches in Humans and Animals", *Circulation*, vol. 81, No. 6 (Jun. 1990) pp. 2007–2012.

Bom et al., "Early and Recent Intraluminal Ultrasound Devices", *International Journal of Cardiac Imaging*, vol. 4 (1989) pp. 79–88.

Schwartz et al., "Intracardiac Echocardiographic Guidance and Monitoring During Aortic and Mitral Balloon Valvuloplasty: In Vivo Experimental Studies", Abstract, *JACC*, vol. 15, No. 2, 104A (Feb. 1990).

Pandian et al., "Real–Time, Intracardiac, Two–Dimensional Echocardiography. Enhamced Depth of Field with a Low–Frequency (12.5 MHz) Ultrasound Catheter", *Echocardiography*, vol. 8, No. 4 (1991) pp. 407–422.

Hung et al., "Usefulness of Intracardiac Echocardiography in Transseptal Puncture During Percutaneous Transvenous Mitral Commissurotomy", Section of Cardiology, Chang Gung Med. Col. and Chang Gung Memorial Hospital, (May 10, 1993) p. 853.

Weintraub et al., "Intracardiac Two–dimensional Echocardiography in Patients with Pericardial Effusion and cardiac Tamponade", *Journal Am Soc. of Echocardiography*, vol. 4, No. 6, (Nov.–Dec. 1991) pp. 571–576.

Schwartz et al., "Intracardiac Echocardiographic Imaging of Cardiac Abnormalities, Ischemic Myocardial Dysfunction, and Myocardial Perfusion: Studies With a 10 MHz Ultrasound Catheter", *Journal Am Soc.of Echocardiography*, vol. 6, No. 4, (Jul.–Aug. 1993) pp. 345–355.

Rothman et al., "Intraluminal Ultrasound Imaging Through a Balloon Dilation Catheter in an Animal Model of Coarctation of the Aorta", *Circulation*, vol. 85, No. 6 (Jun. 1992) pp. 2291–2295.

Tardif et al., "Intracardiac Echocardiography With a Steerable Low–Frequency Linear–Array Probe for Left–Sided Heart Imaging From the Right Side; Experimental Studies" *Journal Am. Soc. of Echocardiography*, vol. 8, No. 2 (Mar.–Apr. 1995) pp. 132–138.

Schwartz et al., "Intracardiac echocardiography without fluoroscopy: Potential of a balloon–tipped, flow–directed ultrasound catheter", *Am. Heart Journal*, vol. 129, No. 3 (Mar. 1995) pp. 598–603.

Kremkau, Frederick, "AAPM Tutorial. Multiple–Element Tranducers", *RadioGraphics*, (Sep. 1993) pp. 1163–1176.

Belohlavek et al., "Three—and Four–Dimensional Cardiovascular Ultrasound Imaging: A New Era for Echocardiography", *Mayo Clin Proc.*, vol. 68 (Mar. 1993) pp. 221–240.

Seward et al., "Multiplane Transesophageal Echocardiography: Image Orientation, Examination Technique, Anatomic Correlations, and Clinical Applications", *Mayo Clin Proc.*, vol. 68 (Jun. 1993) pp. 523–551.

Bom et al., "Intravascular Ultrasound: Newest Branch of the Echo–Tree", *Cardiovascular Imaging*, vol. 4 (1992) pp. 55–59.

Schwartz et al., "Intracardiac echocardiography during simulated aortic and mitral balloon valvuloplasty: In vivo experimental studies", *Am. heart Journal*, vol. 123, No. 3 (Mar. 1992) pp. 665–674.

Seward, et al., "Ultrasound Cardioscopy: Embarking on a New Journey", *Mayo Clin Proc.*, vol. 71, No. 7, (Jul. 1996), pp. 629–635.

Kossoff, et al., "Real–time quasi–three–dimensional viewing in sonography, with conventional, gray–scale volume imaging", *Ultrasound Obstet. Gynecol.*, vol. 4, (1994), pp. 211–216.

Entrekin, et al., "Real–time 3–D ultrasound imaging with a 1–D 'fan beam' transducer array", *SPIE*, vol. 1733 (1992), pp. 264–272.

Smith, et al., "High–Speed Ultrasound Volumetric Imaging System—Part I: Transducer Design and Beam Steering", *IEEE Transactions on Ultrasonics, Ferroelectrics, and Frequency Control*, vol. 38, No. 2 (Mar. 1991), pp. 100–108.

von Ramm, et al., "High–Speed Ultrasound Volumetric Imaging System—Part II: Parallel Processing and Image Display", *IEEE Transactions on Ultrasonics, Ferroelectrics, and Frequency Control*, vol. 38, No. 2 (Mar. 1991), pp. 109–115.

Devonald, et al., "Volume Imaging: Three–Dimensional Appreciation of the Fetal Head and Face", *J. Ultrasound Med.*, vol. 14 (1995), pp. 919–925.

Belohlavek et al., "Toroidal Geometry: Novel Three–Dimensional Intracardiac Imaging with a Phased–Array Transducer", *Journal Am. Soc. of Echocardiography*, vol. 10, No. 5 (Jun. 1997), pp. 493–498.

Lam et al., "Transesophageal Echocardiography with the Use of a Four–Millimeter Probe", *Journal Am. Soc. of Echocardiography*, vol. 10, No. 5 (Jun. 1997), pp. 499–504.

Talbert, D.G., "An 'Ad–On' Modification for Linear Array Real Time Ultrasound Scanners to Produce 3 Dimensional Displays", Conference: Ultrasonics International 1977. Brighton, England (Jun. 28–30, 1997), copy 128/916. pp. 52–67.

Tardif et al., Intracardiac Echocardiography With a Steerable Low–Frequency Linear–Array Probe for Left–Sided Heart Imaging From the Right Side: Experimental Studies:, *Journal Am. Soc. of Echocardiography*, vol. 8, No. 2 (Mar.–Apr. 1995) pp. 132–138.

McCann et al., "Multidimensional Ultrasonic Imaging for Cardiology", *Proc IEEE*, (1988) 76: 1063–1071.

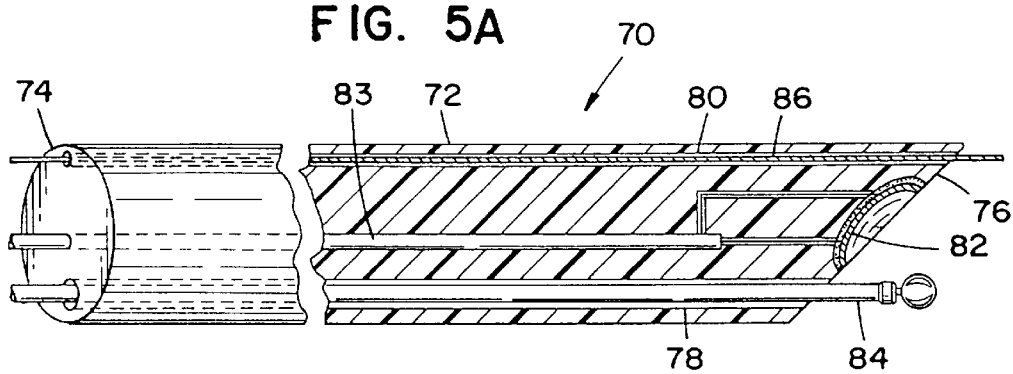
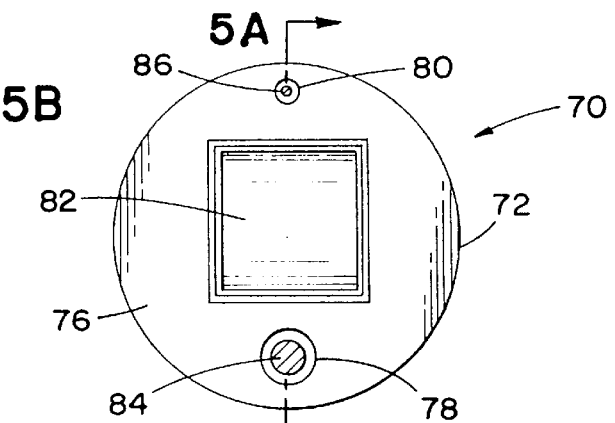
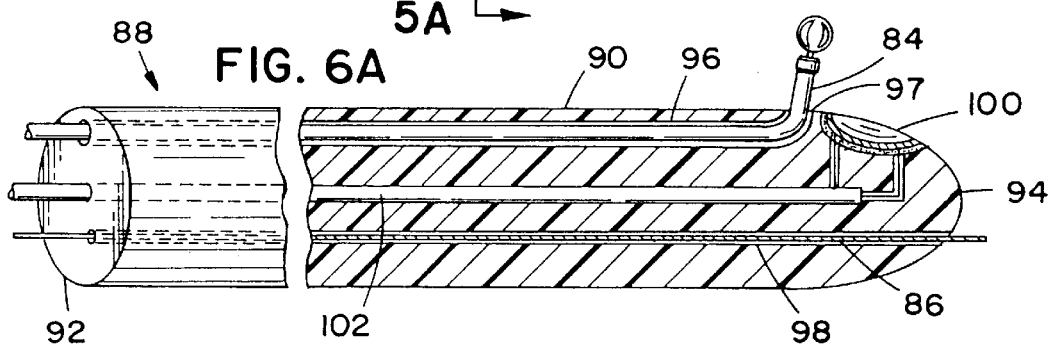
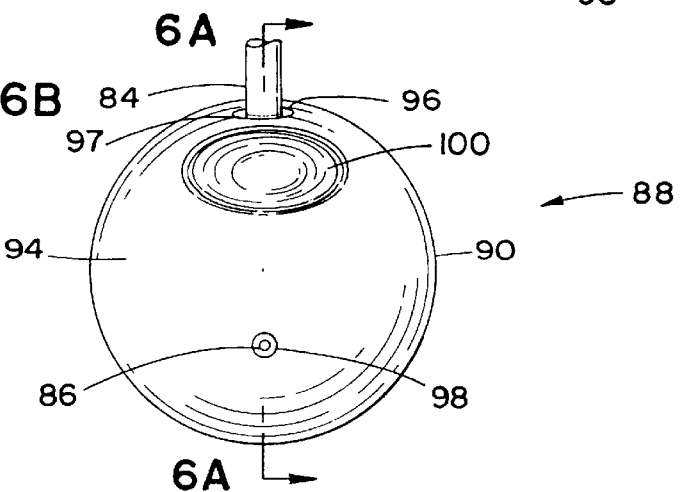

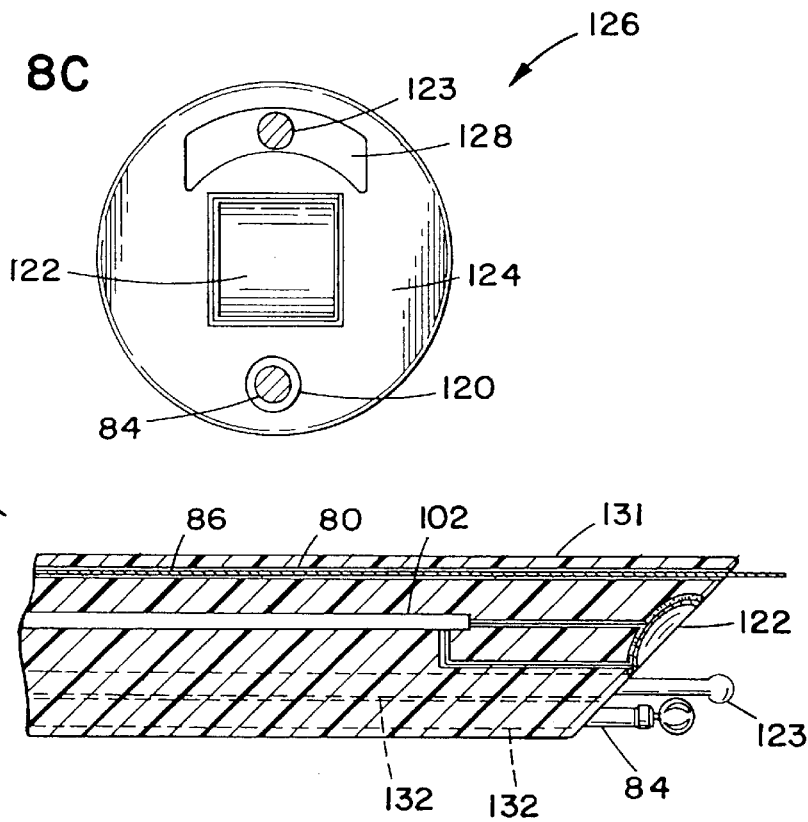
FIG. 8C
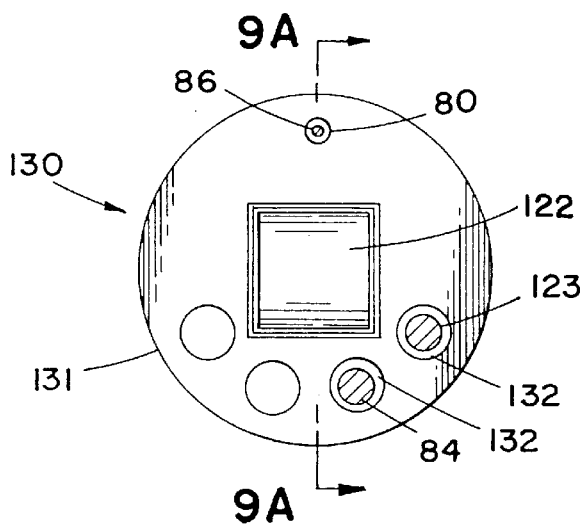
FIG. 9A
FIG. 9B

VOLUMETRIC IMAGE ULTRASOUND TRANSDUCER UNDERFLUID CATHETER SYSTEM

CROSS-REFERENCE TO RELATED APPLICATIONS

This application is a continuation of Ser. No. 08/678,380 filed Jun. 28, 1996, now U.S. Pat. No. 5,704,361 which is a continuation-in-part application of U.S. patent application Ser. No. 08/305,138, filed Sep. 13, 1994 and now abandoned, which is a continuation application of U.S. patent application Ser. No. 07/972,626, filed Nov. 6, 1992, now issued U.S. Pat. No. 5,345,940, which is a continuation-in-part application of U.S. patent application Ser. No. 07/790,580, filed on Nov. 8, 1991, now issued U.S. Pat. No. 5,325,860.

BACKGROUND OF THE INVENTION

Noninvasive ultrasonic imaging systems are widely used for performing ultrasonic imaging and taking measurements. Such systems typically use scan heads which are placed against a patients skin. Exemplary uses for such systems include heart and internal organ examinations as well as examinations of developing fetuses. These systems operate by transmitting ultrasonic waves into the body, receiving echoes returned from tissue interfaces upon which the waves impinge, and translating the received echo information into a structural representation of the planar slice of the body through which the ultrasonic waves are directed.

Catheter based invasive ultrasound imaging systems, typically used for intracardiac or transvascular imaging, are a relatively new addition to ultrasound armamentarian. Conventional underfluid transducers for use on catheters are comprised of crystal arrays (e.g. linear phased array) or a single crystal translated over a surface, producing a tomographic field of view in an azimuthal plane of the array. Typical arrays include: 1) linear array (linear sequential array), usually producing a rectangular or rhomboidal picture; 2) cylindrical array or rotating crystal, producing a round pie-shaped tomographic cut of structures; and 3) sector array (linear phased array), producing a triangular shaped image emanating from a small transducer source. All images are tomographic in nature and are focused in the azimuthal and elevation plane. The intent of having these conventional transducer configurations is to produce a thin ultrasound cut of the insonated structures. Such tomographic planes by nature are thin and of high resolution.

The narrow field of view provided by conventional catheter transducer configurations is problematic because structures lying outside of the plane of view can only be visualized by reorienting or manipulating the catheter. Due to the tortuous and confined nature of a typical catheter pathway, catheter manipulation is impractical and often impossible. Consequently, the localization of specific targets is difficult and at times can be disorienting because of an inability to appreciate contiguous anatomic landmarks.

Advances in 3-dimensional imaging capabilities have been made with respect to non-catheter related ultrasonic imaging systems. For example, U.S. Pat. No. 5,305,756, issued to Entrekin et al., which is hereby incorporated by reference, discloses general 3-dimensional imaging techniques in a non-catheter based context. What is needed is a catheter based imaging system that utilizes 3-dimensional imaging techniques to provide a wide field of view so as to improve anatomic localization for precision underfluid diagnostics and interventions.

SUMMARY OF THE INVENTION

The present invention relates generally to a volumetric, 3-dimensional image ultrasound transducer underfluid catheter system.

The present invention also relates to an ultrasonic and interventional catheter device operated in an intracardiac or transvascular system, with the aid of a volumetric 3-dimensional imaging capability.

In one particular embodiment, the present invention relates to a catheter apparatus comprising an underfluid catheter body having proximal and distal ends. An ultrasonic transducer array is mounted longitudinally along the catheter body proximate the distal end. The transducer array has a volumetric field of view that projects radially/laterally outward from the catheter. Features in such wide volumetric field of view can be imaged, measured, or intervened by an underfluid therapeutic device with an aid of the real-time image.

It is significant that the transducer array described in the previous paragraph has a 3-dimensional field of view. A first dimension, referred to as an azimuthal direction, is aligned with the length of the transducer array. A second dimension, referred to as a depth direction, is the depth into the body which an ultrasonic signal is transmitted and from which an echo return. A third dimension, referred to as an elevation direction, is perpendicular to both the azimuthal and the depth directions.

If the transducer array comprises a linear phased array having a single row of piezoelectric crystals, a 3-dimensional field of view can be generated by focusing the ultrasound signals in the azimuthal direction (parallel to the longitudinal axis of the catheter) and diverging the ultrasound signals in the elevational direction (transverse to the longitudinal axis of the catheter). The ultrasonic signals can be diverged in the elevational direction through the use of lenses. For example, the signals can be diverged by mounting a silicone rubber concave lens or a plastic convex lens in front of the transducer array.

If the transducer array comprises multiple rows of piezoelectric crystals, a 3-dimensional field of view can be generated by electronically phasing the ultrasound signals in both the azimuthal and elevational directions. Of course, lenses can be used in association with multiple row arrays to further widen the field of view.

It will be appreciated that catheters constructed in accordance with the principles of the present invention can optionally include one or more ports that extend longitudinally through the catheter bodies. The ports are preferably adapted for guiding therapeutic instruments through the catheter and preferably have exit ends adjacent to the field of view of the catheter imaging system. In operation, the ports guide the therapeutic instruments such that the operative ends of a therapeutic instruments are directed toward the 3-dimensional field of view of the imaging system.

It will also be appreciated that catheters constructed in accordance with the principles of the present invention can include one or more guidewire ports which extend longitudinally through the catheters and are adapted for receiving guidewires.

One advantage of the present invention is to provide real-time 3-dimensional images of underfluid features so as to visualize contiguous anatomy, such as a large volume of tissues without frequently rotating, flexing, or extending the catheter.

Another advantage is that the present invention provides a much better underfluid "eye"—a 3-dimensional "motion picture"—for an operator when he/she intervenes the underfluid features by using an underfluid therapeutic device. These images provide the operator a direct aid without opening a large area of a body.

A further advantage is that the present invention have numerous clinical applications. One is related to underfluid imaging: There is a considerable need to increase the field of view when imaging from within chambers or blood vessels. The physical space of the chambers or blood vessels is small, and the anatomy in question is closed approximated and usually totally surrounds the transducer. A conventional tomographic presentation provides only a limited slice, thus requiring frequent manipulation of transducer in order to visualize contiguous anatomy. The present invention is a solution to visualizing larger volumes of tissue. The underfluid defocusing transducer array does not appreciably affect the electronics and does not require alteration in the display format. The catheter apparatus is immersed in fluid, a homogeneous, low scattering medium, which is an ideal environment for this particular transducer modification.

Another main clinical application is related to underfluid intervention: In diagnostic and therapeutic procedures, there is an increasing need for volumetric 3-dimensional visualization which would improve anatomic localization and recognition of continuous structures and events.

A further advantage of the present invention is that by using such a catheter system, major surgical procedures can be avoided. It dramatically reduces the patient's physical pain in operation and mental distress after operation due to any large visible scars, etc.

These and various other advantages and features of novelty which characterize the invention are pointed out with particularity in the claims annexed hereto and forming a part hereof. However, for a better understanding of the invention, its advantages and objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

A better understanding of the construction and operational characteristics of a preferred embodiment(s) can be realized from a reading of the following detailed description, especially in light of the accompanying drawings in which like reference numerals in the several views generally refer to corresponding parts.

FIG. 5A shows a partial perspective and cross-sectional view of a first alternate embodiment of a catheter in accordance with the principles of the present invention;

FIG. 5B shows a view of the distal end of the embodiment of the catheter shown in FIG. 5A;

FIG. 6A shows a partial perspective and cross-sectional view of a second alternate embodiment of a catheter in accordance with the principles of the present invention;

FIG. 6B shows a view of the distal end of the catheter shown in FIG. 6A;

FIG. 8C shows a view of the distal end of the catheter shown in FIG. 8A having an alternatively shaped secondary port;

FIG. 9A shows partial perspective and cross-sectional view of a fourth alternate embodiment of a catheter in accordance with the principles of the present invention; and FIG. 9B shows a view of the distal end of the catheter shown in FIG. 9A.

DETAILED DESCRIPTION OF THE PREFERRED EMBODIMENTS

Figure 1:
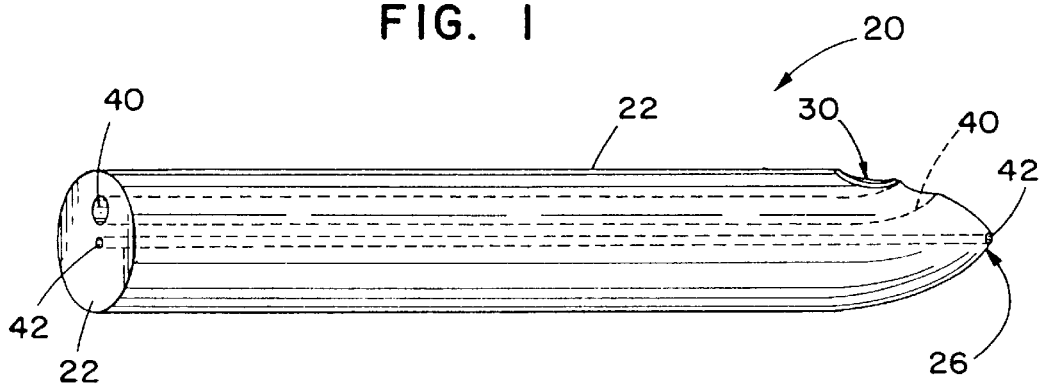
FIG. 1 is a partial perspective view of an embodiment of a catheter in accordance with the principles of the present invention.
Figure 2:
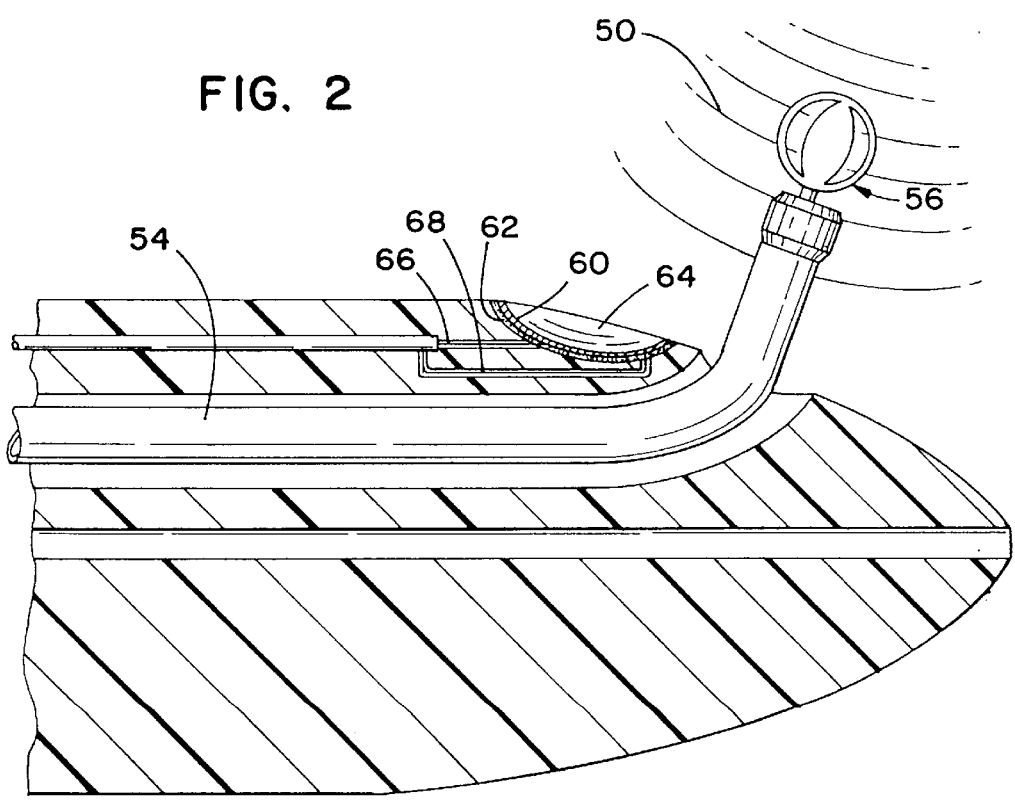
FIG. 2 is an enlarged cross-sectional view taken proximate the distal end of the catheter shown in FIG. 1.
Figure 3:
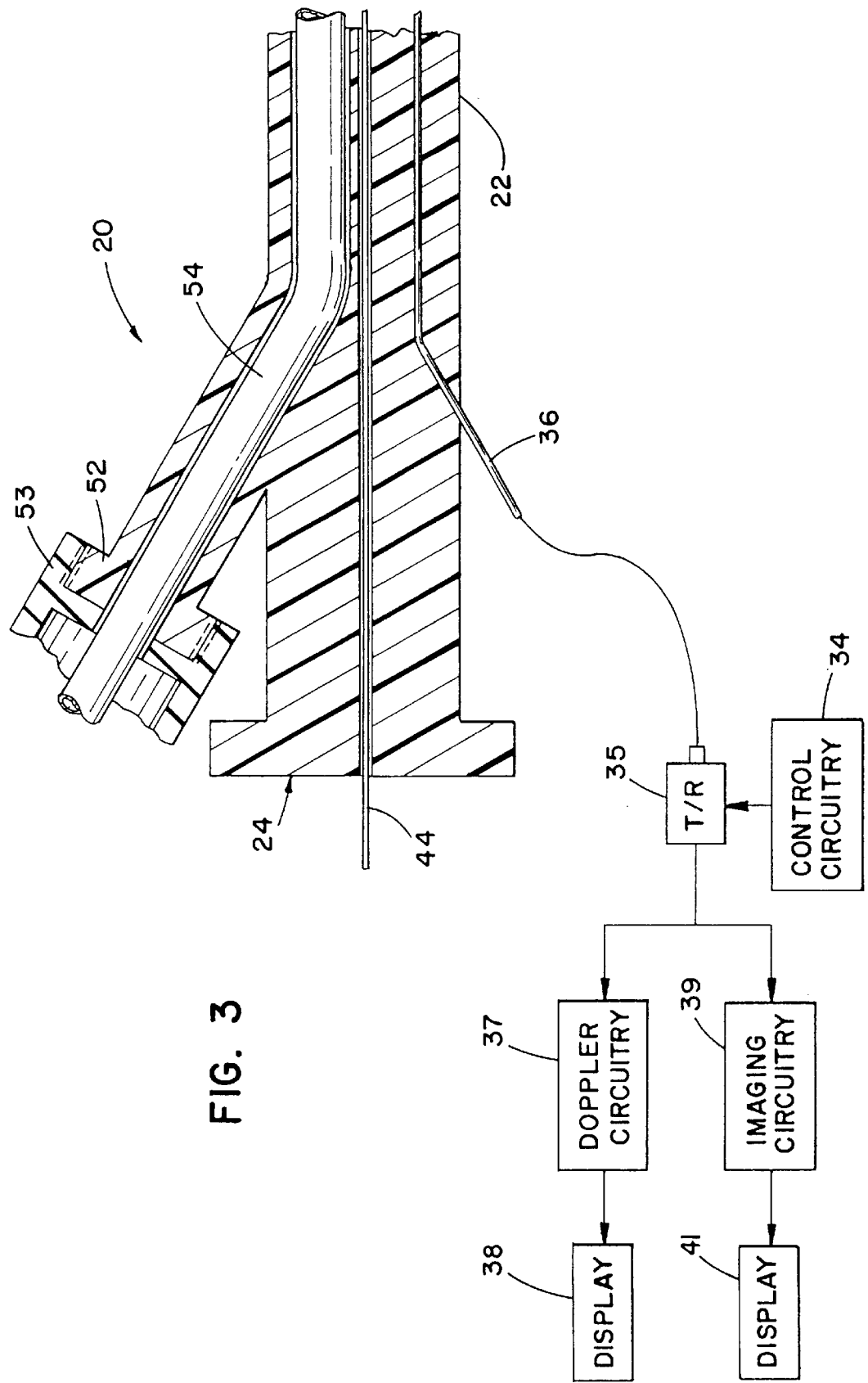
FIG. 3 is a block diagram in part and sectional diagram in part illustrating an embodiment of a system utilizing the catheter shown in FIG. 1.

Referring now to FIGS. 1–3, there is, generally illustrated by reference numeral 20, a catheter in accordance with the principles of the present invention. As shown, catheter 20 includes an elongated flexible or rigid tubular catheter body 22 having a proximal end 24 and a distal end 26. Catheter 20 includes proximate its longitudinal distal end 26 a phased array ultrasonic transducer 30 which is used to transmit ultrasound and receive resultant echoes so as to provide a field of view within which Doppler flow rates can be measured and features imaged. It is appreciated that the other types of ultrasonic transducers can be used in the present invention, such as any mechanical types, or any dynamic array types, or any offset stereoscopic imaging types, or any multidimensional imaging types incorporated into a virtual reality environment for underblood operation, etc. An electrical conductor is disposed in the catheter body 22 for electrically connecting transducer 30 to control circuitry 34 external of catheter body 22. An access port 40 is disposed in catheter body 22 and extends from proximate the proximal end 24 of catheter body 22 to proximate the distal end 26 of catheter body 22. Access port 40 is configured to receive a therapeutic device, such as a catheter, medication, sensors, etc., so as to enable such items to be delivered via access port 40 to distal end 26 of catheter body 22 for operation within the ultrasonic transducer field of view. Such items might be used for intervention; e.g., ablation catheter, surgical device, etc., monitoring blood pressure, sampling blood, etc. A guide wire access port 42 is also disposed within catheter body 22 and extends from proximate proximal end 24 of the catheter body 22 to proximate distal end 26 of catheter body 22 for receiving a guide wire 44.

In the preferred embodiment of the present invention, the ultrasonic transducer preferably has a frequency of 5 to 30 megahertz (MHz) and more preferably a frequency of 7 to 10 MHz. Intracardiac imaging in an adult will require image penetration of up to 2 to 10 centimeters (cm). In the preferred embodiment, catheter body 22 preferably has a diameter of 4 to 24 French (one French divided by Pi equals one millimeter (mm)) and, more preferably, a diameter of 6 to 12 French. In the preferred embodiment, access port 40 has a diameter of 7 to 8 French and guide wire port 42 has a diameter of 0.025 to 0.038 inches.

As generally illustrated in FIG. 3, catheter 20 of the present invention can be utilized in a medical system including the appropriate control circuitry 34 for controlling operation of the ultrasonic transducer. As illustrated in FIG. 3, control circuitry 34 is electrically interconnected to transceiver circuitry 35 (T/R) for receiving and transmitting signals via a cable 36 to ultrasonic transducer 30. In turn, transceiver circuitry 35 is electrically interconnected to Doppler circuitry 37 and an appropriate display device 38 for displaying hemodynamics or blood flow. In addition, transceiver circuitry 35 is electrically interconnected to suitable imaging circuitry 39 which is interconnected to a display 41 for displaying images.

During operation, control circuitry 34 might be designed to cause ultrasonic transducer 30 to vibrate so as to cause an appropriate ultrasound wave to project from proximate the distal end 26 of catheter body 22. The ultrasound wave, represented by lines 50 in FIG. 2, will propagate through the blood surrounding distal end 26 and a portion of the body structure. A portion of the ultrasound wave so transmitted will be reflected back from both the moving red blood cells and the like and the body structures to impinge upon transducer 30. An electrical signal is thereby generated and transmitted by the cable 36 to the input of transceiver 35. A signal might then be transmitted to Doppler circuitry 37 which will include conventional amplifying and filtering circuitry commonly used in Doppler flow metering equipment. Doppler circuitry 37 will analyze the Doppler shift between the transmitted frequency and the receive frequency to thereby derive an output proportional to flow rate. This output may then be conveniently displayed at display 38 which might be a conventional display terminal. Accordingly, the user will be able to obtain a readout of blood flow rates or hemodynamic information.

In order to obtain imaging information, control circuitry 34 will likewise trigger ultrasonic transducer 30 via transceiver 35 to vibrate and produce an ultrasound wave. Once again, a portion of the wave or energy will be reflected back to ultrasonic transducer 30 by the body features. A corresponding signal will then be sent by cable 36 to transceiver circuitry 35. A corresponding signal is then sent to the imaging circuitry 39 which will analyze the incoming signal to provide, at display 41, which also might be a conventional display apparatus, an image of the body features.

This imaging can occur while a therapeutic or surgical device is being used at distal end 26 of catheter 20 within the field of view provided by ultrasonic transducer 30. Accordingly, the user will be able to monitor his/her actions and the result thereof.

As illustrated in FIG. 3, catheter body 22 might include proximate its proximal end 24 a suitable mounting structure 52 to the access port 40. A therapeutic or surgical device structure 53 might be suitably attached to structure 52 by suitable means, e.g., threaded, etc. As illustrated, an elongated cable-like member 54 will extend along access port 40 and slightly beyond distal end 26 of catheter body 22 wherein an operative portion 56 of the surgical tool might be interconnected.

Figure 4A:
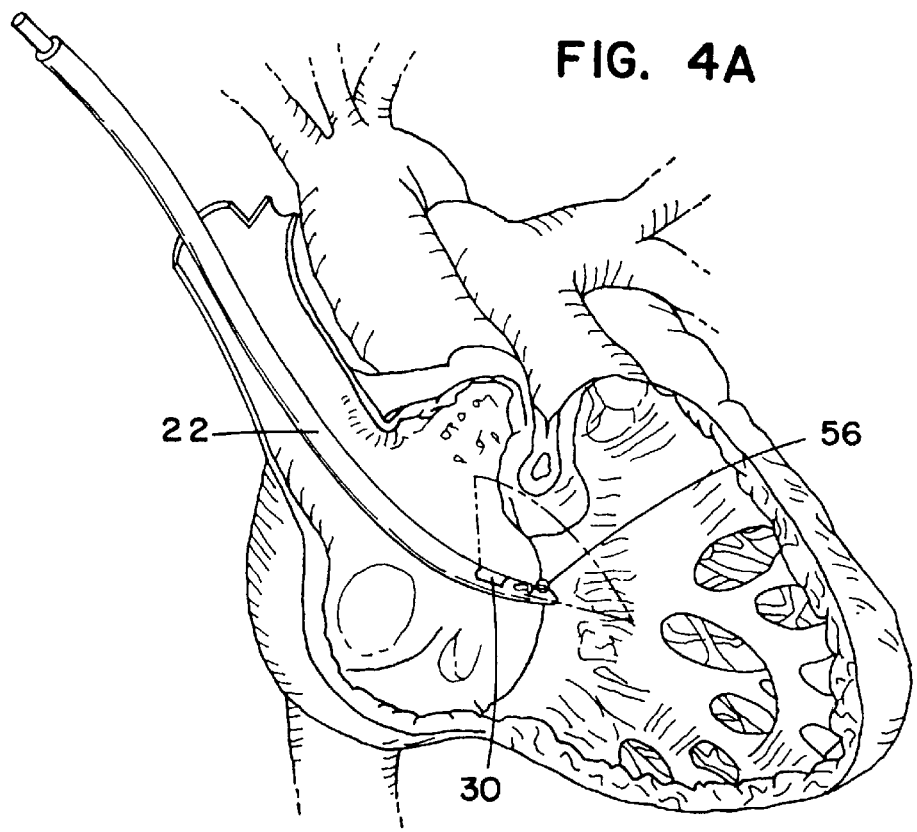
FIG. 4A is an illustration illustrating an application of a catheter in accordance with the principles of the present invention.
Figure 4B:
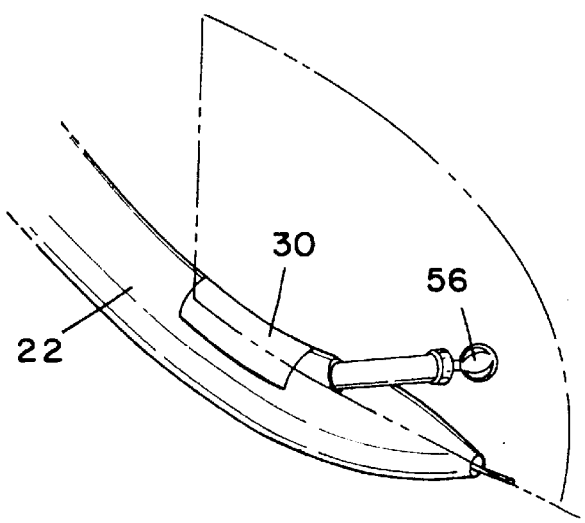
FIG. 4B is a partially enlarged illustration of the catheter shown in FIG. 4A.

Additional detail of distal end 26 of catheter body 22 is illustrated in FIGS. 2, 4A, and 4B. As illustrated in FIGS. 2, 4A, and 4B, ultrasonic transducer 30 might include a piezoelectric polymer, such as Polyvinylidenedifloride (PVDF) 60, which is bonded by an epoxy layer 62 to a depression 64 approximate distal end 26. Although some detail is provided with respect to an embodiment of an ultrasonic transducer which might be used, it will be appreciated that various types of transducers having various configurations and orientations might be utilized in keeping with the present invention.

As illustrated in FIGS. 4A and 4B, the operational portion 56 of the therapeutic device is illustrated as generally being capable of operation in the field of view of ultrasonic transducer 30. Accordingly, it is possible for the user to monitor operation of the therapeutic device by use of the ultrasonic transducer. Moreover, it is possible for the user to monitor the features of the body within the field of view before, during and after interventional activity. It is appreciated that the other types of ultrasonic transducers can be used in the present invention, such as any mechanical types, or any dynamic array types, or any offset stereoscopic imaging types, or any multidimensional imaging types incorporated into a virtual reality environment for underblood operation, etc., so that all forms of field of views, such as 1) tomographic (slices), 2) stereoscopic, 3) three-dimensional, 4) virtual reality (multidimensional) can be provided in the present invention. In addition, it is appreciated that the orientations of the scan array on the catheter can be include side-view, end-view, multiview (two or more views that are moveable or imminently directional transducer referred to in the literature as "omnidirectional"), etc.

FIG. 5A shows a partial cross-sectional view of a first alternative embodiment 70 of the catheter apparatus. The catheter apparatus has an elongated flexible or rigid body 72 having a longitudinal axis and a proximal end 74 and a distal end 76. Disposed proximate a second side of body 72 is a port 78 extending through body 72 from proximate proximal end 74 to proximate distal end 76 of body 72. Port 78 is for receiving and delivering to distal end 76 of body 72 a working tool 84. Working tool 84 shown in the Figures is illustrative only, others types of tools now known or later developed may also be delivered to distal end 76 through port 78. Proximate a first side of body 72 is a guide wire port 80 extending through body 72 from proximate proximal end 74 to proximate distal end 76. Shown in guide port 80 is a guide wire 86.

Distal end 76 is disposed at an oblique angle to the longitudinal axis of body 72, the first side of body 72 extending further in the direction of the distal end than the second side of body 72. An ultrasonic transducer 82, having a first side and a second side, is disposed at an oblique angle to the longitudinal axis of body 72 approximately corresponding to the oblique angle of distal end 76 of body 72. The first side of ultrasonic transducer 82 is disposed proximate the first side of body 72 and the second side of transducer 82 is disposed proximate the second side of body 72. Extending from transducer 82 to proximate proximal end 74 of body 72 is an electrical conductor 83 connecting transducer 82 to control circuitry external of catheter 70, as described with respect to catheter 20 above. Having transducer 82 disposed on an oblique angle toward port 78 allows for easy visualization of tools, such as tool 84, extending beyond distal end 76 of body 72.

FIG. 5B shows a view of distal end 76 of body 72, showing guide wire port means 80, transducer 82, and port means 78.

FIG. 6A shows a partial cross-sectional view of a second alternative embodiment of the catheter in accordance with the present invention, generally referred to as 88. Like first alternative embodiment 70, catheter 88 has an elongated flexible or rigid body 90 having a proximal end 92 and a distal end 94. Catheter 88 also has a port 96 extending through body 90 from proximate proximal end 92 to proximate distal end 94. Port 96 has a distal end 97 proximal distal end 94 of body 90. Distal end 97 of port 96 exits body 90 at an acute angle to a first side of body 90 toward distal end 94. Port 96 is for receiving and delivering to distal end 94 a working tool, such as working tool 84. Catheter 88 also has a guide wire port 98 extending through body 90 from proximate proximal end 92 to proximate distal end 94. Guide wire port 98 is for receiving a guide wire 86.

Also shown in FIG. 6A is a transducer 100 disposed to a first side of body 90 between distal end 94 and distal end 97 of port 96. Extending from transducer 100 to proximate proximal end 92 of body 90 is an electrical conductor 102 disposed in the catheter body 90 for electrically connecting transducer 100 to control circuitry external of the catheter. With transducer 100 disposed to the first side of body 90 and distal end 97 of port 96 exiting body 90 at an acute angle relative to the first side of body 90 toward distal end 94, working tools extending from distal end 97 of port 96 will be within the field of view of transducer 100.

FIG. 6B shows a view of distal end 94 of catheter 88, as shown in FIG. 6A.

Figure 7A:
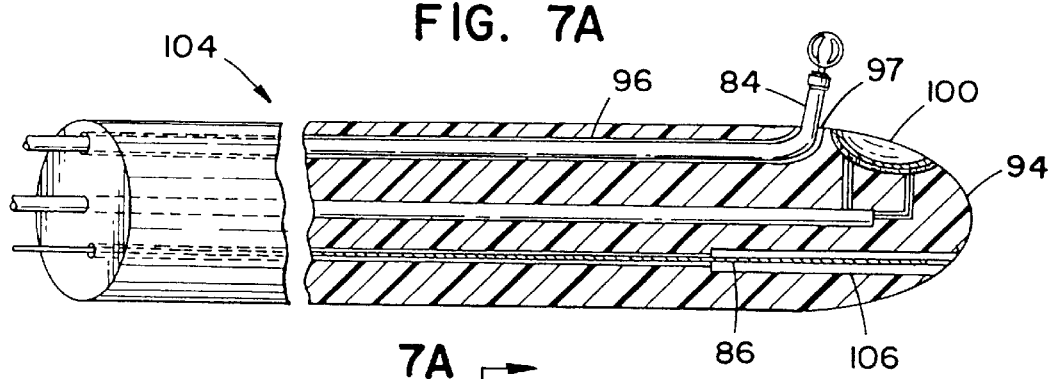
FIG. 7A shows a partial perspective and cross-sectional view of a variation of the second alternate embodiment of the catheter shown in FIG. 6A.
Figure 7B:
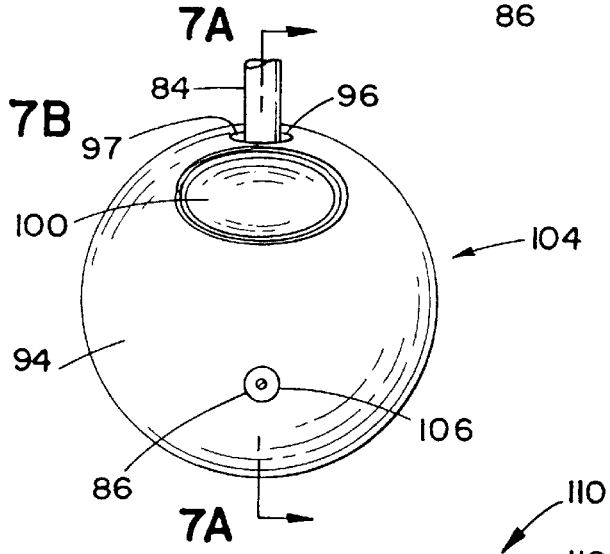
FIG. 7B shows a view of the distal end of the embodiment of the catheter shown in FIG. 7A.

FIG. 7A shows second alternative embodiment 104, as shown in FIG. 6A, except instead of having a guide wire port 98, this variation of the second alternative embodiment 104 has a deflection wire guidance system 106 for manipulating distal end 94. FIG. 7B shows a view of distal end 94 of the catheter shown in FIG. 7A.

Figure 8A:
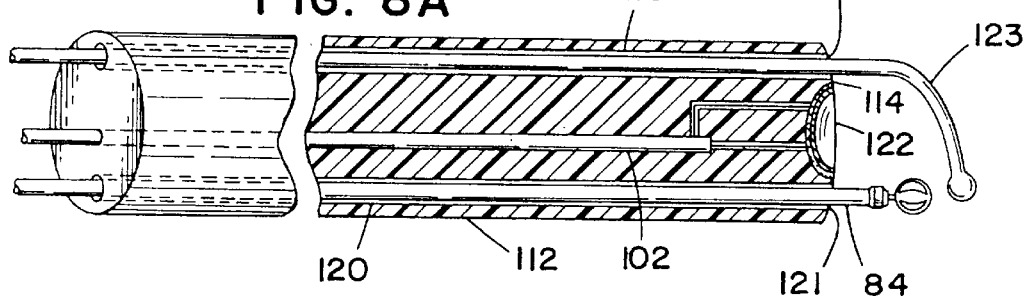
FIG. 8A shows a partial perspective and cross-sectional view of a third alternate embodiment of a catheter in accordance with the principles of the present invention.

FIG. 8A shows a third alternative embodiment 110 of the catheter in accordance with the present invention. Third alternative embodiment 110 has a body 112 having a distal end 114 and proximal end. Disposed proximate a first side of body 112 is a primary port 118 extending through body 112 from proximate proximal end 116 to proximate distal end 114. Primary port 118 has a distal end 119 proximate distal end 114 of body 112 oppositely disposed from primary port 118, proximate a second side of body 112 is a secondary port 120 extending through body 112 from proximate proximal end 116 to proximate distal end 114. Secondary port 120 has a distal end 121 proximate distal end 114 of body 112.

Mounted proximate distal end 114 of body 112 is a transducer 122. Extending from transducer 122 through body 112 to proximate proximal end is an electrical conductor for electrically connecting the transducer 122 to control circuitry external of the catheter. Transducer 122 is disposed between distal ends of primary and secondary ports 119 and 121, respectively. With working ports 118 and 120 oppositely disposed on either side of transducer 122, it is possible to conduct two simultaneous applications, such as holding an object with a first tool disposed through one port and operating on the object held by the first tool with a second tool disposed through the other port. A typical working tool 123 and working tool 84 are shown disposed within ports 118 and 120.

Figure 8B:
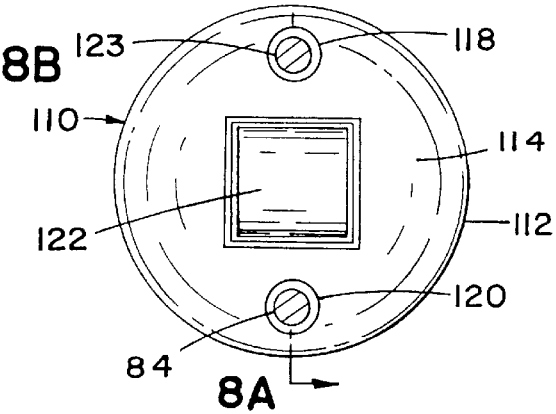
FIG. 8B shows a view of the distal end of the catheter shown in FIG. 8A.

Although the third alternative embodiment of the catheter 110 of the present invention does not include a guide wire port means, a guide wire could be used in primary port 118 or secondary port 120 to initially position catheter 110. Then the guide wire could be retracted from port 118 or 120 and a working tool introduced. FIG. 8B shows a view of distal end 114 of catheter 110.

FIG. 8C shows a view of a distal end 124 of a catheter 126 substantially like catheter 110 shown in FIG. 8A and FIG. 8B, except that catheter 126 has a primary port 128 having an arc-like shaped cross-section, rather than a circular shaped cross-section. Although a circular cross-section has been shown in the Figures for the various ports described herein, the size and shape of the ports can be varied without departing from the principals of the present invention.

FIG. 9A shows a fourth alternative embodiment of a catheter 130 of the present invention. Catheter 130 is similar to catheter 70 shown in FIG. 5A and FIG. 5B except that a plurality of ports 132 are disposed proximate a second side of flexible body 131, rather than one port 78, as shown in FIG. 5A. With a plurality of ports, it is possible, for example, to use a therapeutic tool through one port while simultaneously suctioning and removing debris through another port; or a therapeutic tool can be used through one port while simultaneously electrophysiologically monitoring, suctioning and/or biopsying through a second port, third or fourth port.

The use of the catheter of the present invention is described with respect to the preferred embodiment 20. It is understood that the use of alternative embodiments 70, 88, 110, 126 and 130 is analogous. In use, the user would insert flexible catheter body 22 into the body via the appropriate vascular access to the desired location in the body, such as selected venous locations, heart chamber, etc. In one approach, a guide wire might be first inserted into place and then the catheter body fed along the guide wire. The user might then insert a surgical device into the body through access port 40 and feed the surgical device to proximate distal end 26 of catheter body 22. Prior to, during and after operation of the surgical device, the user might obtain both hemodynamic measurements and images from the ultrasonic transducer field of view. By operation of the surgical device within the field of view of transducer, the user can monitor operation of the surgical device at all times.

I. Detailed Features of the Disclosed Catheters

A. Frequency Agility Ultrasound Frequency

Frequency agility refers to the ability of a transducer to send and receive at various frequencies, most commonly 3, 5, and 7 MHz. It is also appreciated that a single frequency from a single transducer device can be sent and received. In general, higher frequencies are used to image fine detail of more proximal or closely related objects while lower frequency transducers scan more remote objects with less detail. The proposed device optimally uses a 5 to 20 mHz transducer with the most optimally applied frequency of 7 to 10 mHz. The lower frequency used in the UIHC reflects the need to image larger objects such as the cardiac septa, valves, and extravascular anatomy.

B. Catheter Size

Catheter diameters will generally be larger than intravascular catheters and will range 4 to 24 French with the optimal catheter diameter 6 to 12 French (French size= French divided by Pi plus millimeter diameter).

C. Intervention

One primary function of this catheter system is to guide the logical and safe use of various a) ablation, b) laser, c) cutting, occluding, e) etc., catheter-based interventional tools. The invention has the access port through which other technologies (devices) can be passed. Once the interventional tool exits the catheter tip, it can be directed repeatedly and selectively to specific site for controlled intervention.

D. Imaging

The invention is also an imaging system capable of visualizing intracardiac, intravascular, and extravascular structures. Because the transducer frequencies utilized are usually lower than intravascular systems, the catheter 20 can see multiple cardiac cavities and visualize structures outside the vascular system. The imaging capability is basically two-fold: 1) diagnostic and 2) application.

1. Diagnostic imaging: The catheter 20 can effectively perform diagnostic intracardiac and transvascular imaging. This application will more than likely be performed just prior to an interventional application. The intervention then will follow using the same catheter system and its unique delivery capability. Some examples of diagnostic imaging include 1) accurate visualization and measurement of an intracardiac defect, 2) characterization of valve orifice, 3) localization of a tumor and its connections, 4) etc. Extravascular diagnoses would include 1) visualize pancreatic mass/pathology, 2) retroperitoneal pathology, 3) intracranial imaging, 4) recognition of perivascular pathology, and 5) imaging of other fluid containing space such as urinary bladder, bile system, fluid filled orifice or cavity (e.g. filled saline), etc.

2. Application imaging refers to the use of the catheter and its imaging capability to deliver and then apply another technology such as 1) occlusion device for closure of a septal defect, 2) ablation catheters for treatment of bypass tracts, 3) creation of a defect such as that with the blade septostomy catheter or laser-based catheter system, and 4) directing of valvuloplasty (such as prostrate surgery, placement of stents, gallstone removal etc.), etc. By direct imaging of an application, such as ablation, the procedure will be able to be performed more safely and repeatedly, and the result can be better assessed.

E. Hemodynamics

The catheter 20 is a truly combined ultrasound Doppler and conventional hemodynamic catheter. There are Doppler catheters, and there are catheters capable of imaging and measuring hemodynamic pressure. However, the catheter 20 is capable of Doppler hemodynamics (continuous and pulsed wave Doppler) as well as high-fidelity hemodynamic pressure recording while simultaneously imaging the heart and blood vessel. The catheter 20 provides a combination of imaging, hemodynamic, and interventional delivery catheter.

II. Analogy with Other Existing Therapeutic Technologies

Like interventional peritoneoscopy, intracardiac ultrasound is capable of 1) imaging, 2) delivering a therapeutic device, and 3) obtaining simultaneous hemodynamics which can be used to develop less invasive cardiac surgical techniques. This simultaneous use of one or more devices within the heart or vascular tree opens up the potential to develop less invasive surgical therapies. Examples would include 1) removal of a cardiac tumor by visually grasping the tumor with one device and visually cutting its attachment with a second device, thus allowing less invasive extraction of intracardiac mass lesions, 2) visually placing an electrophysiologic catheter on a bypass tract and then with direct ultrasound visualization ablate the underlying tract with the second device, 3) visually performing laser surgery such as creating an intra-atrial defect, vaporization of obstructing thrombus such as is seen in pseudointimal occlusion of conduits, 4) visually removing a foreign body from the heart or vascular tree, and 5) directing intravascular surgery from within a blood vessel or monitoring concomitant hemodynamic changes.

III. Selected Applications Include the Following

A. Radio-Frequency Ablation

Presently a bypass tract is localized by an electrophysiologic study which systematically maps the atrioventricular valve annulus. Positioning of the ablation catheter is determined by x-ray fluoroscopy and certain electrical measurements which relate the distance of the ablation catheter from a reference catheter. The catheter 20 will allow an operator to map the atrioventricular valve under direct ultrasound visualization. Thus, increased accuracy of catheter placement, precision of the applied therapy, and immediate assessment of outcome would result.

The above ablation technique would be particularly applicable for right-sided bypass tracts (in and around the tricuspid valve annulus). This would be accomplished by placement of the catheter 20 through the superior vena cava above the tricuspid annulus.

For left-sided bypass tracts, the catheter 20 could be placed across the atrial septum under direct ultrasound visualization. The mitral annulus could thus be mapped directly and the localized bypass tract precisely ablated under visual ultrasonic and hemodynamic direction. Complications such as valve perforation, multiple imprecise applications of ablation energy, and inadvertent ablation of normal conduction tissue would be substantially reduced.

Ablation of bypass tracts would be an ideal utilization of the proposed ultrasonic interventional catheter system.

B. Cardiac Biopsy

In the era of safe cardiac biopsy, there is a need for precision biopsy. Ultrasound direction of the biopsy device to an intracardiac tumor, avoidance of scar, and selective biopsy of suspect tissue are feasible with the catheter 20 device. One of the more frequently life-threatening complications in the cardiac catheterization laboratory is catheter perforation of the heart. Such complications most commonly accompany cardiac biopsy, electrophysiologic catheter manipulation, and valvuloplasty. Use of an intracardiac ultrasound imaging, hemodynamics, and delivery catheter should substantially increase or improve safety of these procedures.

C. Transvascular Diagnoses

The catheter 20 will allow visualization of perivascular and extravascular pathology. Transvascular or transorgan imaging and localization of pathology out of the immediate vascular tree will result in a substantial step forward in the diagnosis and possible treatment of difficult to reach pathology. The catheter 20 cannot only diagnose but guide a biopsy needle and therapeutic device to an extravascular lesion in question. The retroperitoneum, mediastinum, and basal cerebrovascular pathology are logical areas of interest. Accurate characterization of various pathologies will be more feasible. Every organ has its own vascular system, and the proposed ultrasound transvascular system is an ideal tool to assess difficult to reach areas of the body. The vascular system is a conduit to each organ, and the catheter 20 can be delivered to each organ. Characterization of the underlying parenchyma and possible transvascular biopsy or treatment will ultimately be developed.

D. Ultrasound Manipulation of Therapeutic Devices Within the Heart and Blood Vessels The catheter 20 opens the potential not only to visualize but to directly intervene with the same catheter system. There are numerous intraoperative catheter-based systems which to date use conventional x-ray to accomplish their goal of placement and application of a specified therapy. There is a need for a device which can more precisely guide such catheter-based systems. It is too expensive and technically impractical to incorporate ultrasound into every catheter based technology. The catheter 20 has all the prerequisites of an ideal imaging and interventional instrument and has the ability to 1) image, 2) obtain hemodynamics by multiple means (pressure dynamics and Doppler), 3) function as a diagnostic as well as therapeutic device, and 4) accommodate other unique technologies which would enhance the application of both systems.

E. General Applications

It is anticipated that intravascular, transvascular, and intracardiac devices could be delivered through the port means described above within or about the heart and blood vessels of the body. The catheters described above, however, could also be used in any ectogenic tissue, such as liver, parenchyma, bile ducts, ureters, urinary bladder, and intracranial—i.e., any place in the body which is echogenic which would allow passage of a catheter for either diagnostic or therapeutic applications using ultrasound visualization.

F. Expanding Applications of Technologies

The catheter 20 is a new and exciting innovation to invasive medicine. There are multiple other and yet-to-be-determined applications. However, the new concept described opens the potential development of less expensive, more precise, and safe intravascular and transvascular diagnostic and surgical devices.

IV. Summary

The catheter 20 is very much different from any conventional ultrasound catheter-based system. The catheter 20 incorporates image and hemodynamic capability as well as the ability to deliver other diverse technologies to specified sites within the cardiovascular system (heart and blood vessels). The catheter 20 is seen as an ideal diagnostic and therapeutic tool for future development. The proposed applications foster greater preciseness, adaptability, and safety. Ultrasound permits visualization from within blood-filled spaces as well as through blood-filled spaces into other water- or fluid-filled tissue. The catheter 20 will evolve into the ultimate interventional system.

FIG. 4A is an illustration showing one potential use of the ultrasound imaging and hemodynamic catheter (UIHC). In this particular example, the UIHC is advanced from the superior vena cava to the tricuspid valve annulus. Simultaneously visualized in the annulus, electrophysiologic and ultimately and ablation procedure are performed. The ability to directly visualize and direct therapeutic catheter devices highlights only one of the many applications of the UIHC.

Figure 10:
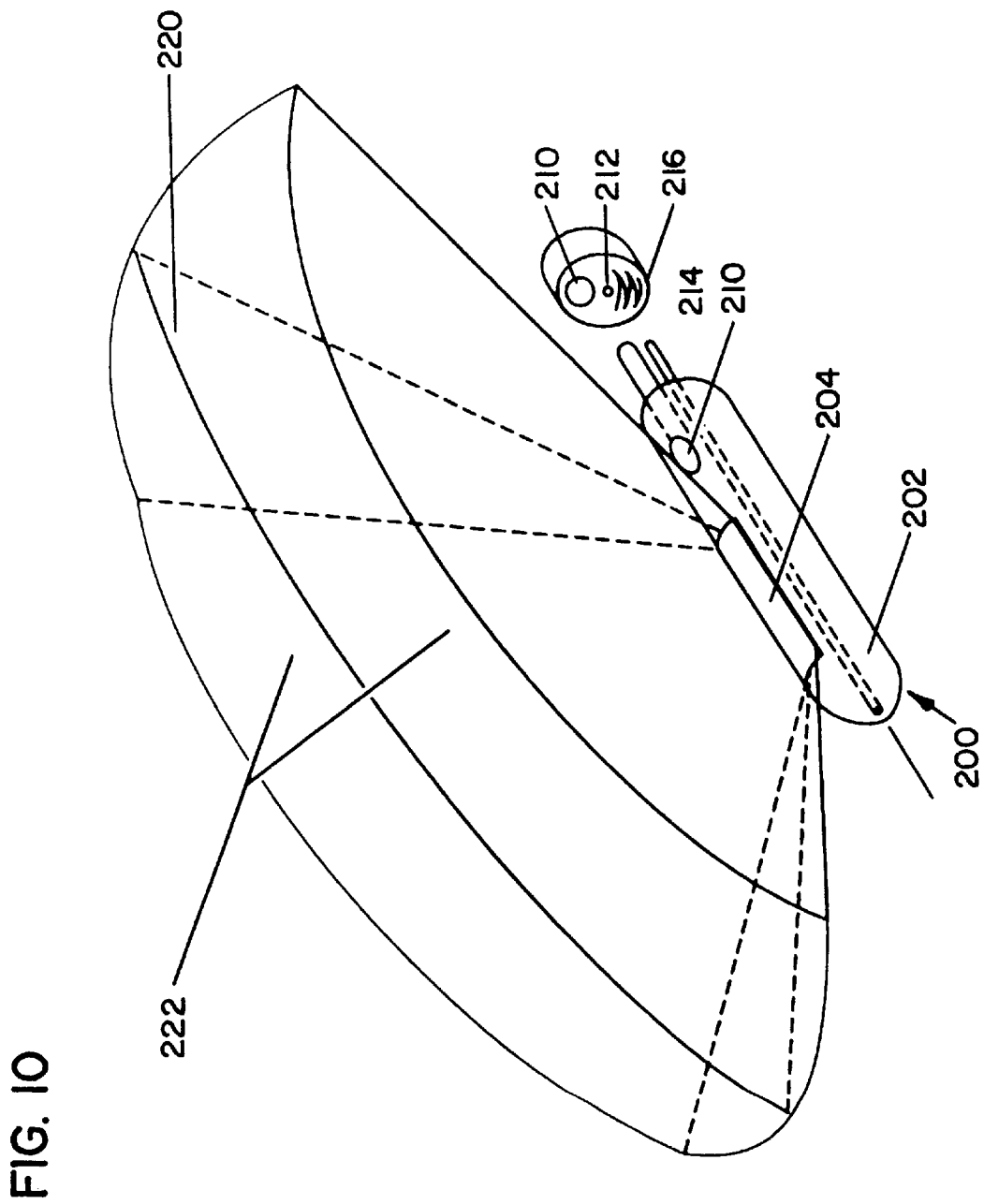
FIG. 10 is a partial schematic view of an embodiment of an underfluid catheter system in accordance with the principles of the present invention.

Another embodiment of the catheter system, generally in accordance with the principles of the present invention is shown in FIG. 10, which is designated as reference numeral 200. The catheter system 200 has a catheter body 202 and an ultrasonic transducer array 204 mounted on proximate the distal end of the catheter body 202. It is appreciated that other parts of the catheter system can be similar to those in the catheter systems 20, 70, 88, 104, 110, and 130 as shown in FIGS. 1, 5A, 6A, 7A, 8A, and 9A, respectively. For the purpose of illustration and explanation, FIG. 10 shows a partial schematic view of the catheter system 200.

Figure 11:
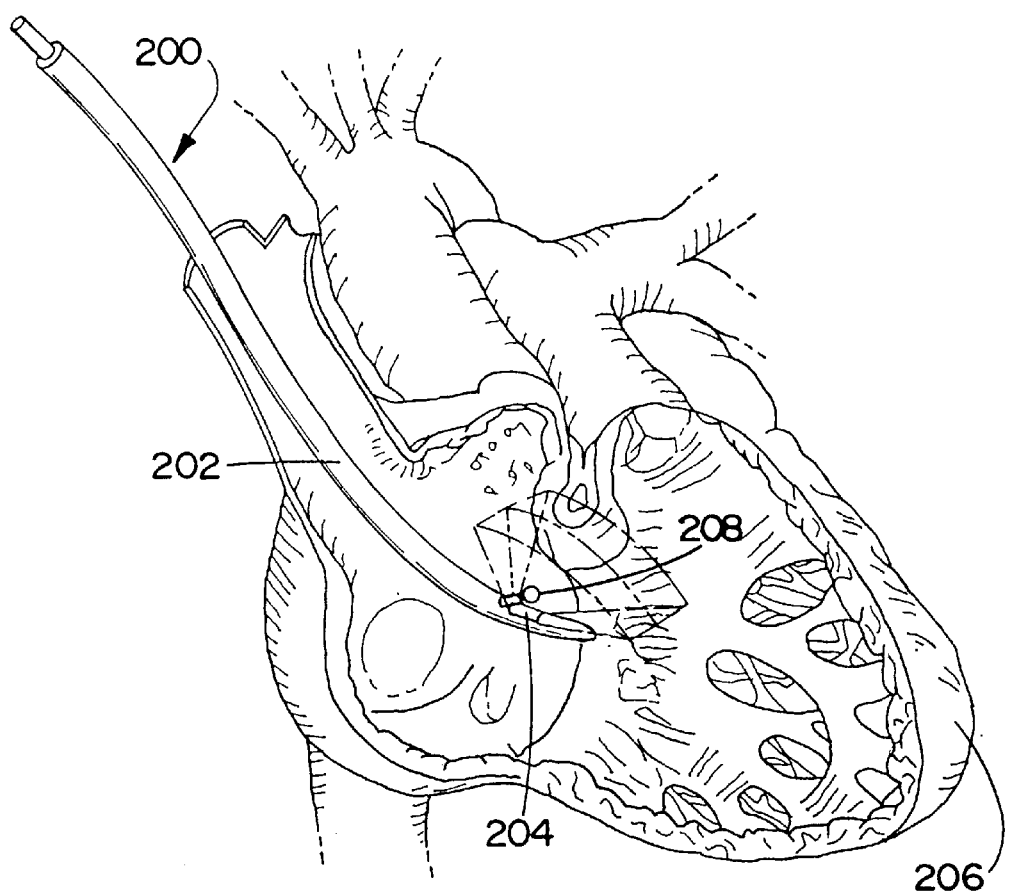
FIG. 11 is an enlarged view illustrating the catheter system operated underfluid with an aid of a volumetric field of view.
Figure 12:
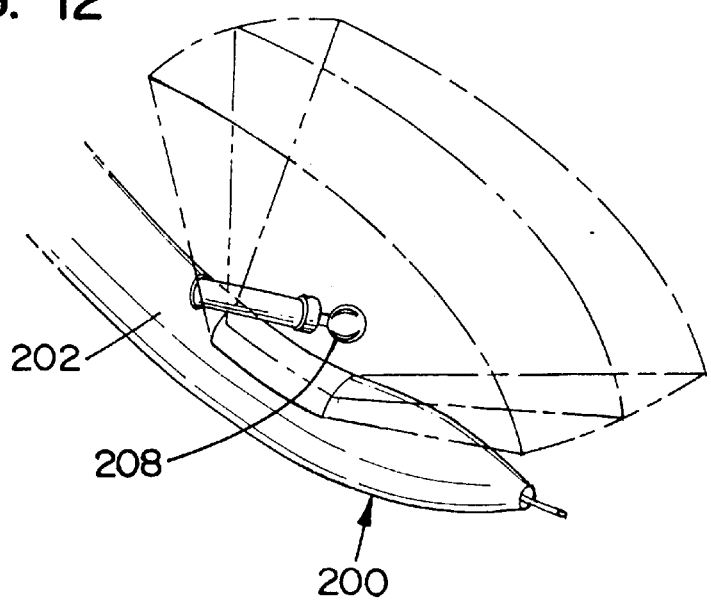
FIG. 12 is an enlarged perspective view illustrating the catheter system providing a volumetric field of view.

In FIG. 11, the catheter body 202 of the catheter system 200 is inserted into an underfluid cavity of a body 206. In FIG. 12, a therapeutic device 208 projects from the catheter system 200 proximate the distal end of the catheter system 200 and manipulates features in the cavity of the body 208. This manipulation is under observation of a 3-dimensional image shown on a display, which can be similarly connected to the ultrasound transducer array as shown in FIG. 3, outside the body 208 proximate the proximal end of the catheter system 200.

Likewise, the underfluid catheter body 202 has tool port 210 disposed in the catheter body 202 extending from proximate the proximal end to proximate the distal end of the catheter body 202 for receiving the therapeutic device 208, such as a catheter, medication, sensor, surgical device, etc., so as to enable such items to be delivered via the tool port to proximate the distal end of the catheter body 202. It will be appreciated that the tool port is optional. It will also be appreciated that additional tool ports can be disposed in the catheter body 202. The therapeutic device 208 is projected into an underfluid environment, as shown in FIGS. 11–12, and operated therein with the aid of a volumetric 3-dimensional image of the underfluid environment and the therapeutic device 208.

Further, the catheter system 200 can also optionally include a guidewire port 212 disposed in the catheter body 202 extending from proximate the proximal end to proximate the distal end of the catheter body 202 for receiving a guide wire 214. The guide wire 214 guides the catheter body 202 when inserting into a body, such as the body 206.

Further, the catheter system 200 includes a control circuit which can be similar to the control circuitry 34 shown in FIG. 3. The control circuitry 34 is used to control the operation of the ultrasonic transducer array 204. The control circuitry 34 is electrically interconnected to a transceiver circuitry 35 (T/R) for receiving and transmitting signals via a cable 36 to ultrasonic transducer array 204. In turn, the transceiver circuitry 35 is electrically interconnected to a measuring circuitry, such as the Doppler circuitry 37, which is interconnected to a first display 38 for displaying hemodynamics, blood flow, etc. In addition, the transceiver circuitry 35 is electrically interconnected to an imaging circuitry 39 which is interconnected to a second display 41 for displaying a 3-dimensional image of the underfluid environment.

As shown in FIG. 10, the catheter body 202 can also house some encased electronics 216.

In the preferred embodiment of the present invention, the ultrasonic transducer array 204 is mounted on a side of the catheter body 202. The array 204 can also be mounted on the tip of the catheter body 202. The catheter body 202 is a flexible catheter capable of manual or electronic interactive flexible tip. The guidewire port 212 has a diameter of 0.035 inches. It is appreciated that the range of the diameter of the guidewire port 212 can be varied from 0.025 to 0.038 inches. The tool port 210 for transporting the therapeutic device 208 is a 7 French port. It is appreciated that the range of the tool port 210 can be varied from 3 French to 20 French.

Figure 13:
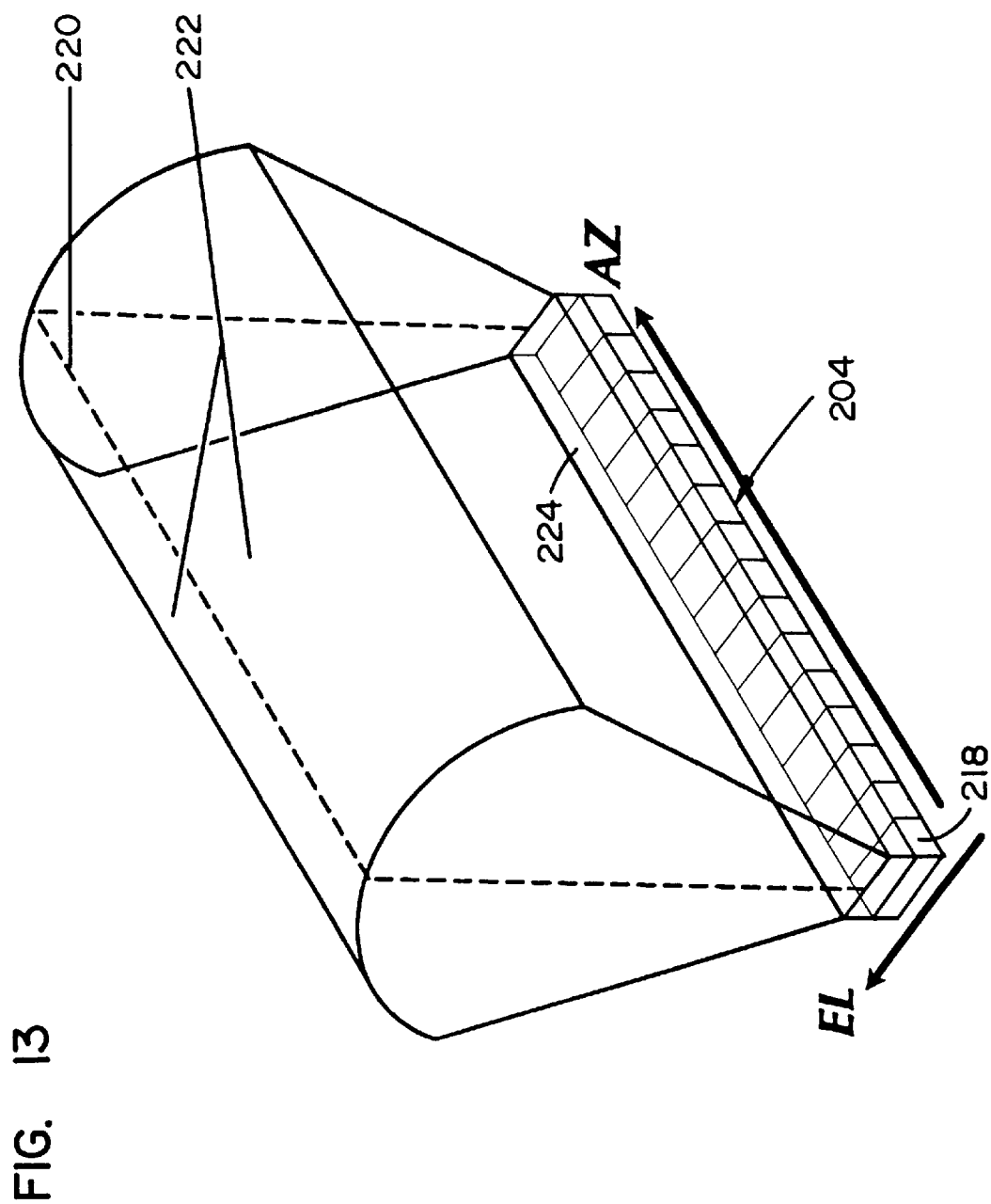
FIG. 13 is an enlarged perspective view of an ultrasonic transducer array having a single row of crystals covered by a lens which provides a volumetric field of view.

As shown in FIG. 13, the ultrasonic transducer array 204 is comprised of a single row of individual crystals 218. Each crystal 218 is arranged side by side. A field of view generated by the ultrasonic transducer array 204 has a primary tomographic plane 220 in azimuthal dimension along an AZ axis. The row of the array 204 is parallel to the AZ axis. An elevation axis (EL) is perpendicular to the AZ axis. A primary beam from the ultrasonic transducer array 204 lies in the primary tomographic plane 220. The primary beam has usually a sector configuration (generally a fan or triangle shape) or a linear configuration (generally rectangular shape).

The volumetric field of view can be produced by defocusing the primary tomographic plane 220 such that a plurality of elevation planes 222 spread laterally outward from the primary tomographic plane 220. The primary tomographic plane 220 and the elevation planes 222 together form a volumetric field of view. To defocus the primary tomographic plane 220 as shown in FIG. 13, a lens 224 is placed on the top of the ultrasonic transducer array 204. The ultrasound beams which are usually collimated are defocused along the elevation direction (EL) after the beams go through the lens 224 (or other lenses 226,228 as shown in FIGS. 16 and 17).

The lenses 224, 226, or 228 are preferred to be made from materials such as a plastic material or silicone rubber. It is appreciated that other types materials can be used to make the lens.

Figure 16:
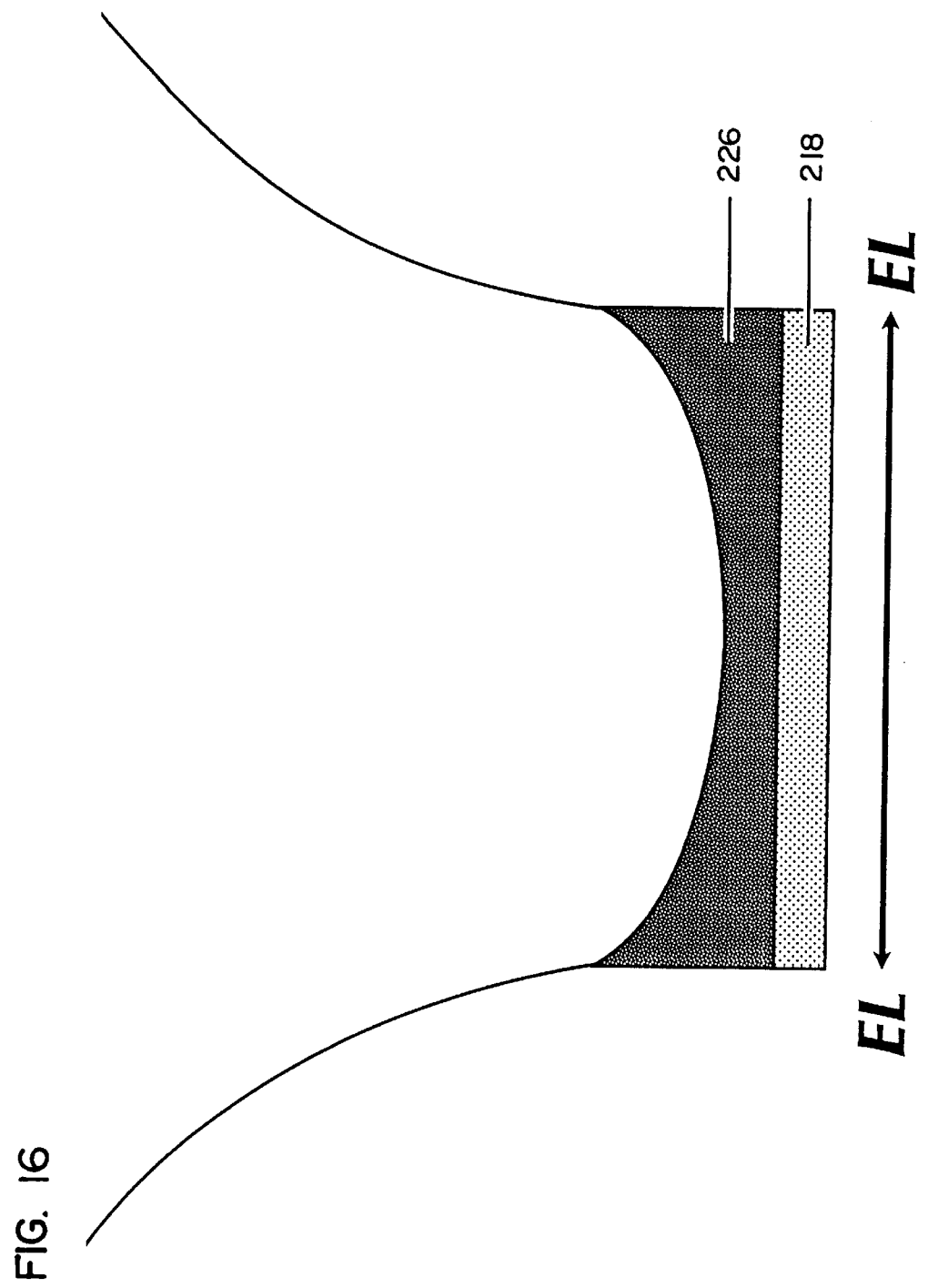
FIG. 16 is an enlarged schematic cross-sectional view of a concave silicone rubber lens being placed on the ultrasonic transducer array, providing an outwardly defocused ultrasound beam.

In FIG. 16, the lens 226 is a concave lens, preferably made of silicone rubber, which transmits ultrasound waves slower than the surrounding environment, such as body tissues. The ultrasound waves pass through the lens 226 and then impact on the body tissues. The speed of the ultrasound waves is slower in the lens but faster in tissue (e.g. 1,540 m/sec). Accordingly, the transmitted ultrasound waves, after passing through more slowly transmitted lens 226 and striking faster transmitted body tissues, will be directed outward. As a result, the collimated ultrasound beams are defocused in the elevation dimension.

Figure 17:
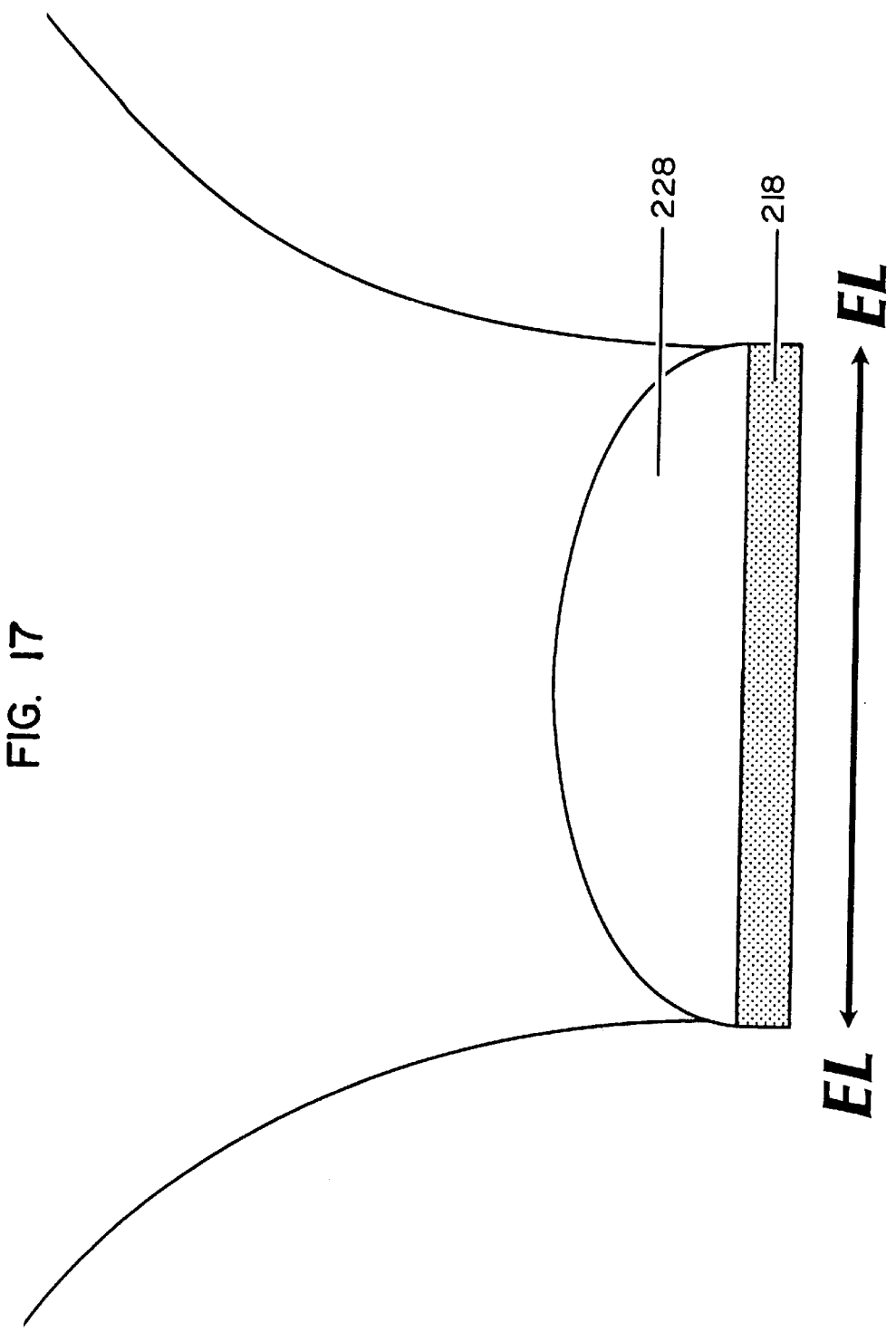
FIG. 17 is an enlarged schematic cross-sectional view of a convex plastic lens being placed on the ultrasonic transducer array, providing an outwardly defocused ultrasound beam.

The defocusing can also be achieved by placing a convex lens 228 on the ultrasonic transducer array as shown in FIG. 17. The convex lens 228, preferably made of plastic, transmits ultrasound waves faster than the surrounding environment, such as body tissues. The ultrasound waves pass through the convex lens 228 and then impact on the body tissues. The ultrasound beams are pulled outward due to the faster velocity in the convex lens 228. As a result, the ultrasound beams are defocused in the elevation dimension.

Figure 18:
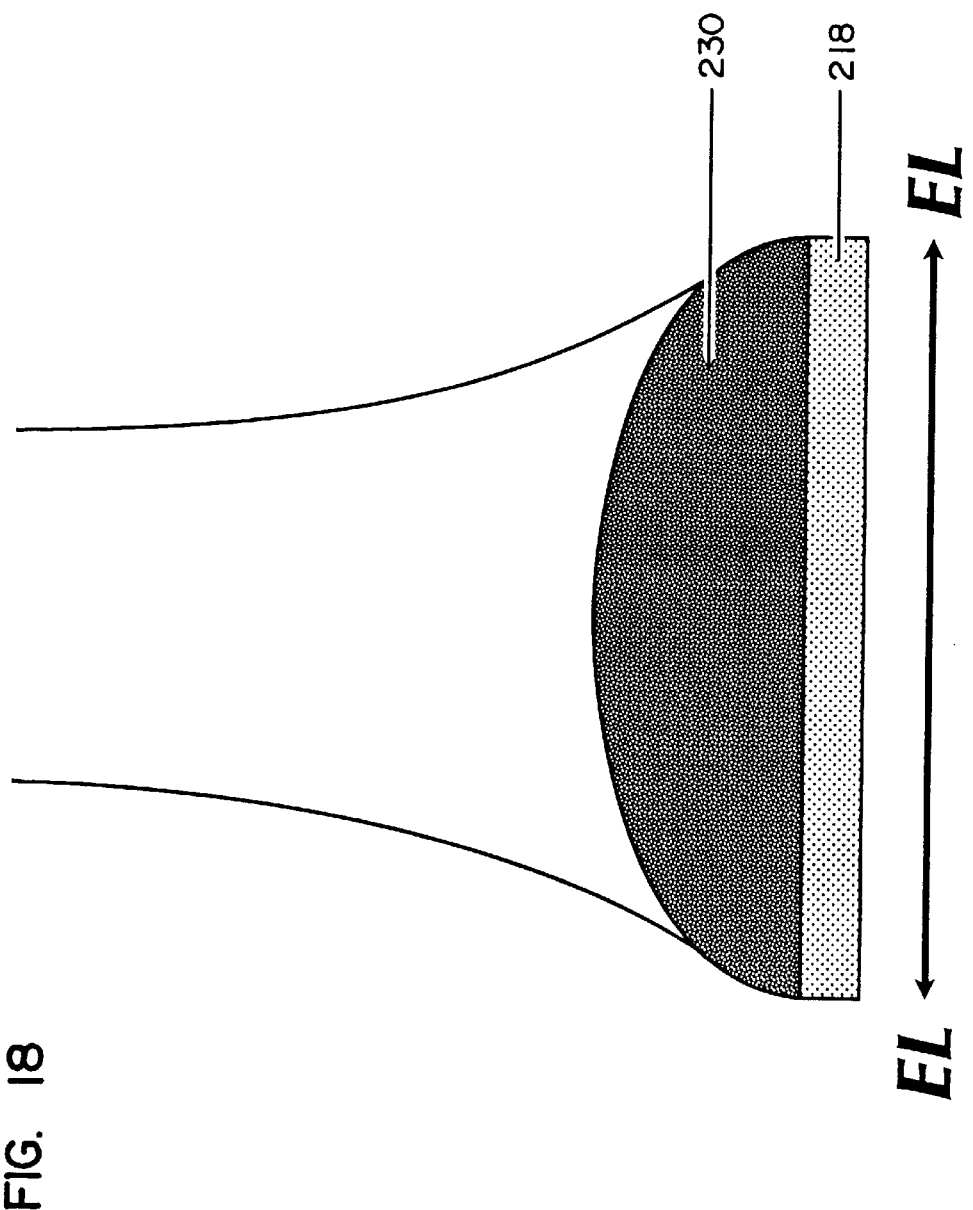
FIG. 18 is an enlarged schematic cross-sectional view of a convex silicone rubber lens being placed on the ultrasonic transducer array, providing an inwardly focused ultrasound beam.

FIG. 18, on the other hand, demonstrates a way of using a lens 230 to, in fact, focus the beams from the transducer array. The collimated ultrasound beams are generated from the ultrasonic transducer array. The convex lens 230 transmits ultrasound waves slower than the surrounding environment, such as body tissues, do. Accordingly, the ultrasound beams are pulled inward due to the faster velocity in body tissues. As a result, the ultrasound beams are focused toward the primary tomographic plane 220.

Figure 14:
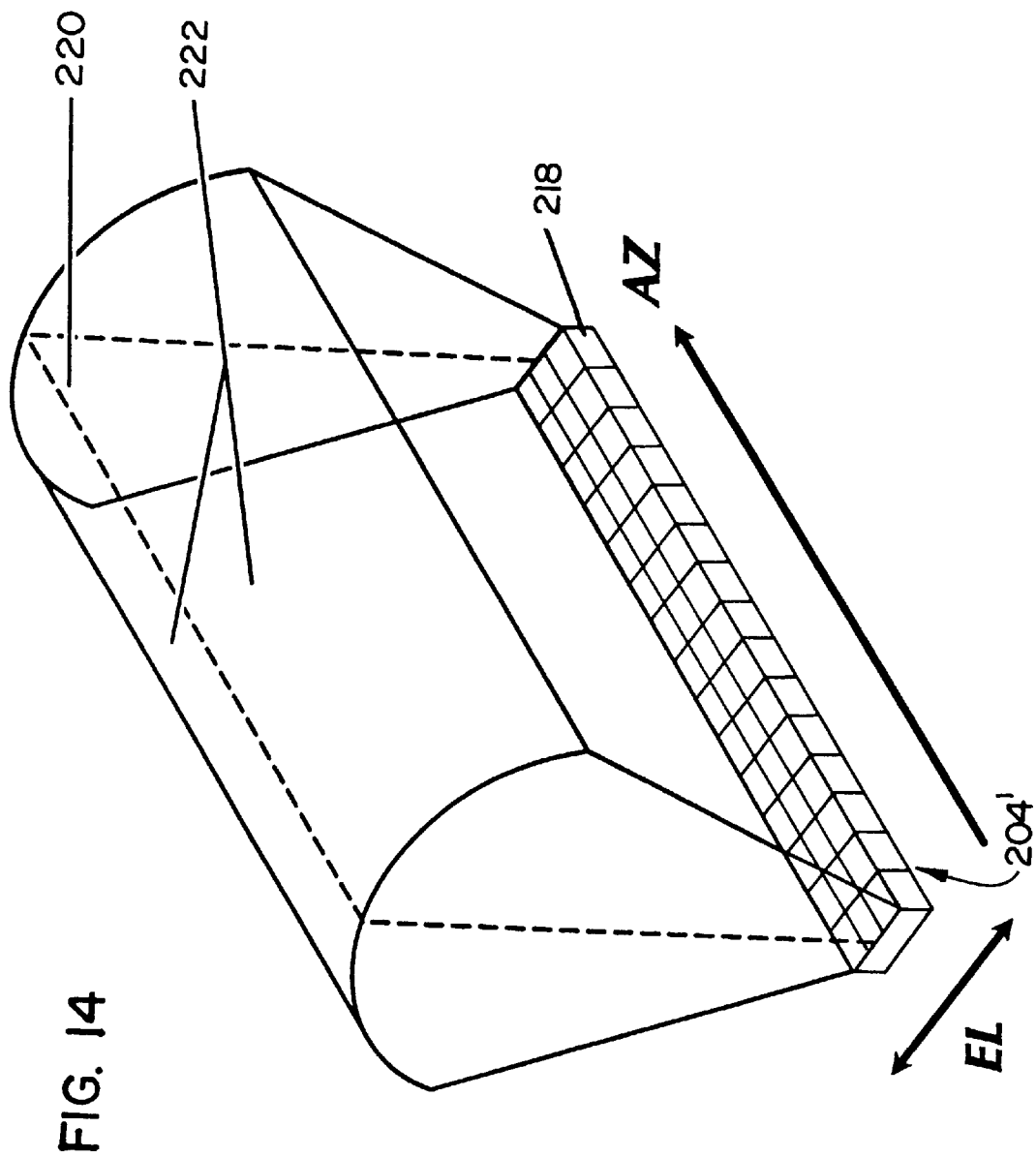
FIG. 14 is an enlarged perspective view of an alternative ultrasonic transducer array having multiple rows of crystals which provides a volumetric field of view.

FIG. 14 shows an alternative embodiment of ultrasonic transducer array 204' which is comprised of multiple rows of individual piezoelectric crystals 218. The rows of the array 204' are parallel to the AZ axis. The columns of the array 204' are parallel to the elevation dimension along the EL axis, which is perpendicular to AZ axis. This type of array is also called volumetric one and one-half (1 and ½) dimensional array. The "elevation" image and the ultimate 3-dimensional image are the result of phasing the crystals in the elevation direction as well as in the azimuthal direction.

Figure 15:
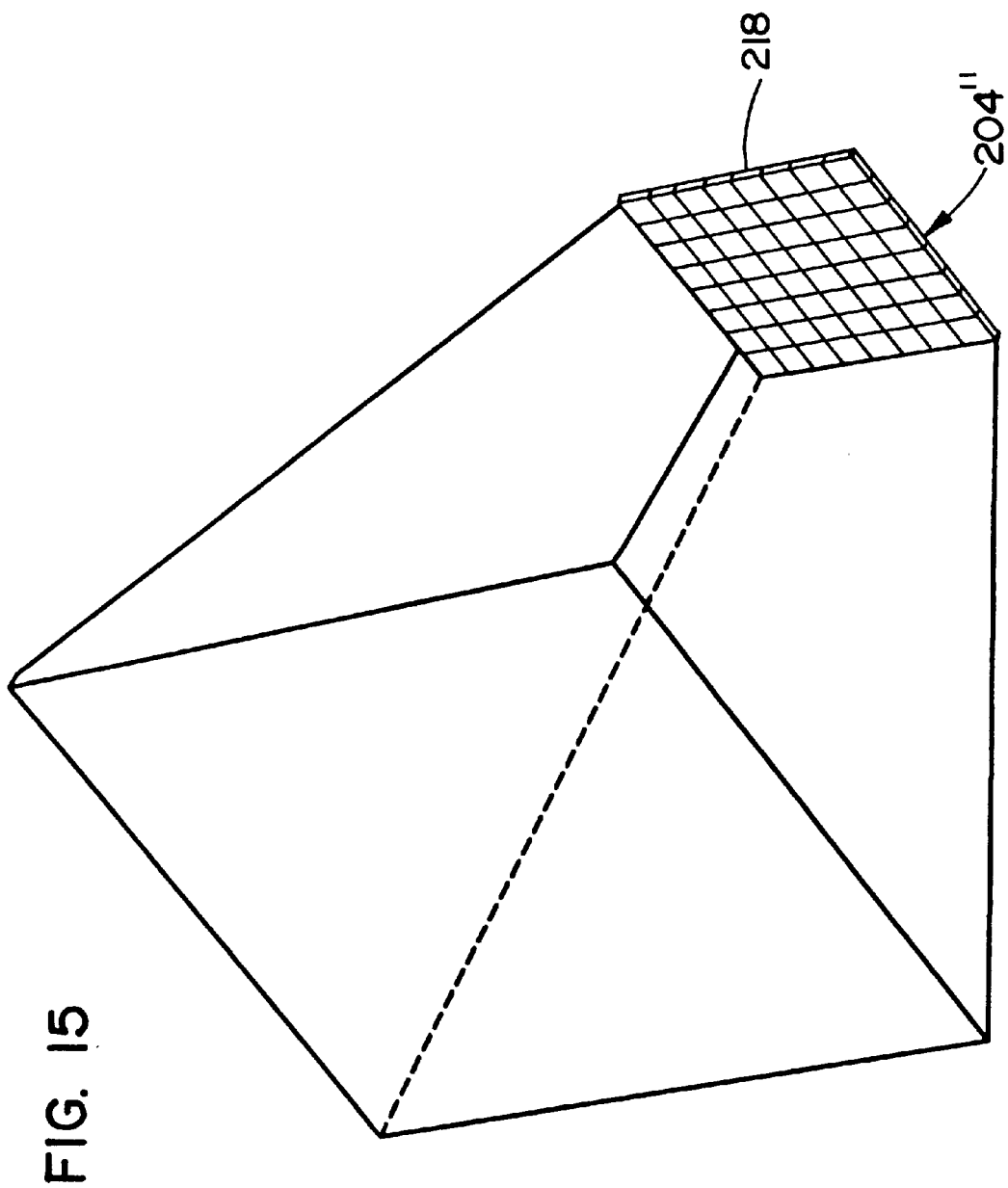
FIG. 15 is an enlarged perspective view of a second alternative ultrasonic transducer array having equal number of rows and columns of crystals which provides a volumetric field of view.

FIG. 15 shows a second alternative embodiment of ultrasonic transducer array 204" which is comprised of equal number of crystals 218 in all dimensions. Similar to the one and one-half (1 and ½) dimensional array 204', the rows of the array 204" are parallel to the AZ axis, and the columns of the array 204" are parallel to the EL axis. This type of array is also called a two (2) dimensional array. The "elevation" image and the ultimate 3-dimensional image are the result of phasing the crystals in the EL direction as well as the AZ direction.

Accordingly, the volumetric field of view as shown in FIGS. 14–15 provides 3-dimensional images of structures under observation. Further, the volumetric field of view not only shows, for example, a primary tomographic cut, but also volumes of features, such as tissue.

In the embodiments of FIGS. 14 and 15, it will be appreciated that no lens is required to generate a volumetric image. Consequently, the ultrasonic beams are focused in both the azimuthal and elevational directions. The volumetric image is generated because the arrays of FIGS. 14 and 15 are 2 dimensional. As a result, a volumetric image can be generated by electronically phasing and steering the ultrasonic impulses in both the azimuthal and the elevational directions.

In the preferred embodiment, the ultrasound transducer is a 7–10 MHz sector array transducer. It is appreciated that the range of the sector array transducer can be varied from 3.7 MHz to 30 MHz.

It is also appreciated that the lenses 224, 226, 228, 230 can be made of different materials which will have variable effects on the transmitted ultrasound beams. By using such defocusing lens, a 3-dimensional image can be seen on a 2-dimensional display outside the body 206 in a real-time operation. Elevation defocusing in using a lens does not interfere with the inherent frame rate or adversely affect conventional echo data.

The lens can also be fabricated to reduce the strength of the dominant tomographic plane (AZ plane). One means of accomplishing this is by changing the attenuation characteristics of the lens so as to reduce the tomographic effect and enhance the volumetric effect of the insonated and displayed object.

The lens is optional, for example, as shown in FIGS. 14 and 15 whereby the beams are phased in both the azimuthal and elevational planes.

The present invention has numerous clinical applications. One of which is the underfluid imaging when imaging from within chambers, cavities or blood vessels. Since the physical space is small, and the anatomy in question is closely approximated and usually totally surrounds the transducer, a 3-dimensional imaging is a solution to visualizing larger volumes of underfluid tissue. In this imaging application, the defocusing lens or electronically controlled phasing in both the azimuthal and elevational directions (i.e., using multi-dimensional arrays such as 1-½ dimensional or 2 dimensional arrays) produces volumetric images. Working port(s) and guidewire(s) are optional. Further, catheter lengths and transducer frequencies are variable.

Another application, when the working port is optionally used in the catheter, is to intervene or manipulate an underfluid structure, such as cutting an underfluid tissue, etc., by a therapeutic device, such as the therapeutic devices 50, 84, 123, 208 shown in FIGS. 4B, 5A, 8A, and 12, respectively. Under such direct volumetric visual guidance, diagnostic and therapeutic procedures can be performed with better spatial orientation.

Another application, when the guidewire is optionally used in the catheter, is to measure some underfluid features, such as blood flow, etc. The measurement can also be performed under direct volumetric visual guidance in the present invention.

Other generic applications include Doppler blood flow determination, color flow imaging, etc.

Thus, the preferred embodiment of the present invention has been described in detail. It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A catheter apparatus, comprising:

an elongated body having a longitudinal axis;

an ultrasonic transducer array having at least one row of ultrasonic transducer elements mounted on the body, each of the ultrasonic transducer elements of the array being operated together as a part of the array for transmitting ultrasonic signals to form a three-dimensional image; and an electrical conductor disposed in the body for electrically connecting the array to a control circuitry.

2. A catheter apparatus of claim 1, wherein the elongated body includes at least one internal channel extending from a proximal end to a distal end of the elongated body.

3. A catheter apparatus of claim 2, wherein the at least one internal channel is a port for delivering a therapeutic device to the distal end of the elongated body.

4. A catheter apparatus of claim 2, wherein the at least one internal channel is a guide wire port.

5. A catheter apparatus of claim 1, wherein the ultrasonic transducer array is an offset stereoscopic imaging ultrasound transducer array.

6. A catheter apparatus of claim 1, wherein the ultrasonic transducer array includes a piezoelectric polymer material.

7. A catheter apparatus of claim 1, wherein the ultrasonic transducer array includes a polyvinylidenedifloride (PVDF) material.

8. A catheter apparatus of claim 1, wherein the control circuitry is external of the elongated body.

9. A catheter apparatus of claim 1, wherein the ultrasonic transducer array is a phased array.

10. A catheter apparatus of claim 1, wherein the at least one row of ultrasonic transducer elements are longitudinally mounted on the body.

11. A catheter apparatus of claim 1, further comprising a lens mounted on the ultrasonic transducer array for defocusing ultrasound beams, at least some of the beams being directed laterally outward which are perpendicular to the longitudinal axis of the body, providing a real time three-dimensional image.

12. A catheter apparatus of claim 1, wherein the ultrasonic transducer array includes a plurality of rows of ultrasonic transducer elements, the ultrasonic transducer elements being phased in both an elevation direction of the array as well as an azimuthal direction of the array, providing a real time three-dimensional image.

13. A catheter apparatus of claim 1, wherein the ultrasonic transducer array includes equal numbers of rows and columns of ultrasonic transducer elements, the ultrasonic transducer elements being phased in both an elevation direction of the array as well as an azimuthal direction of the array, providing a real time three-dimensional image.

14. A catheter apparatus of claim 1, further comprising a therapeutic device delivered via the body for operation within a field of view of the imaging so as to allow visualization of therapeutic device during the operation.

15. A catheter apparatus of claim 1, wherein the ultrasonic transducer array has a frequency of 5 to 30 MHz.

16. A catheter apparatus of claim 1, wherein the ultrasonic transducer array has a frequency of 7 to 15 MHz.

17. A catheter apparatus of claim 1, wherein the catheter body has a diameter of 4 to 24 French.

18. A catheter apparatus of claim 1, wherein the catheter body has a diameter of 6 to 12 French.

19. A catheter apparatus of claim 1, wherein the catheter body has a diameter of 7 to 8 French.

* * * * *